US005770373A

United States Patent [19]
Britschgi et al.

[11] Patent Number: 5,770,373
[45] Date of Patent: Jun. 23, 1998

[54] RAPID AND SENSITIVE DETECTION OF ANTIBIOTIC-RESISTANT MYCOBACTERIA USING OLIGONUCLEOTIDE PROBE SPECIFIC FOR RIBOSOMAL RNA PRECURSORS

[75] Inventors: Theresa B. Britschgi; Gerard A. Cangelosi, both of Seattle, Wash.

[73] Assignee: Becton Dickinson and Company, Franklin Lakes, N.J.

[21] Appl. No.: 745,638

[22] Filed: Nov. 8, 1996

Related U.S. Application Data

[60] Division of Ser. No. 485,602, Jun. 7, 1995, which is a continuation-in-part of Ser. No. 261,068, Jun. 16, 1994, abandoned.

[51] Int. Cl.$^6$ .................................................. C12Q 1/68
[52] U.S. Cl. .................................. 435/6; 435/29; 435/32
[58] Field of Search .................................. 435/6, 29, 32; 536/24.32

[56] References Cited

U.S. PATENT DOCUMENTS

| | | | |
|---|---|---|---|
| 5,288,611 | 2/1994 | Kohne | 435/6 |
| 5,376,527 | 12/1994 | Robson et al. | 435/6 |
| 5,422,242 | 6/1995 | Young | 435/6 |
| 5,612,183 | 3/1997 | Kohne | 435/6 |

FOREIGN PATENT DOCUMENTS

| | | |
|---|---|---|
| 531798 | 3/1993 | European Pat. Off. . |

OTHER PUBLICATIONS

Kempsell, K.E., et al., *J. Gen. Microbiol.* 138:1717–1727 (1992).
Ji, Y., et al., *Microbiology* 140:123–132 (1994).
King, T.C., et al., *Microbiol. Rev.* 50(4):428–451 (1986).
Srivastava, A.K., et al., in *The Ribosome: Structure, Function, and Evolution*, W.E. Hill, et al. (Eds.), American Society for Microbiology, Washington DC, pp. 426–434 (1990).
King, T.C., et al., *J. Biol. Chem.* 258(19):12034–12042 (1983).
Van Ness, J. and Chen L., *Nucl. Acids Res.* 19(19):5143–5151 (1991).
Van Ness, J., et al., *Nucl. Acids Res.* 19(12):3345–3350 (1991).
Cangelosi, G.A., et al., *Molecular and Cellular Probes* 8:73–80 (1993).
Watanabe, S.M., et al., *J. Clin. Microbiol.* 28:319–323 (1990).
Stahl, D.A. and Urbance, J.W., *J. Bacteriology*, 172(1):116–124 (1990).
Pernodet, J., et al., *Gene*, 79:33–46 (1989).
Rogall, T., et al., *International Journal of Systematic Bacteriology*, 40(4):323–330 (1990).
Frothingham, R. and Wilson, K.H., *J. of Bacteriology*, 175(10):2818–2825 (1993).
Van Der Vliet, G.M.E., et al., *J. General Microbiology*, 139:2423–2429 (1993).
Frothingham, R. and Wilson, K.H., *J. of Infectious Diseases*, 169:305–312 (1994).
Frothingham, R., et al., *Journal of Clinical Microbiology*, 32(7):1639–1643 (1994).
Gabrielle et al., Antimicrobial Agents and Chemotherapy 38(9):1959–1965, Sep. 1994.

*Primary Examiner*—Kenneth R. Horlick
*Attorney, Agent, or Firm*—David W. Highet, Esq.

[57] ABSTRACT

The invention relates to methods and oligonucleotide probe compositions useful for determining antibiotic resistance in Mycobacteria. Included are methods for freeing intact precursor ribosomal RNA from mycobacterial cells and for assaying the levels of pre-rRNA in the cells. Also claimed are methods useful in discovering new anti-mycobacterial therapeutic agents.

6 Claims, 6 Drawing Sheets

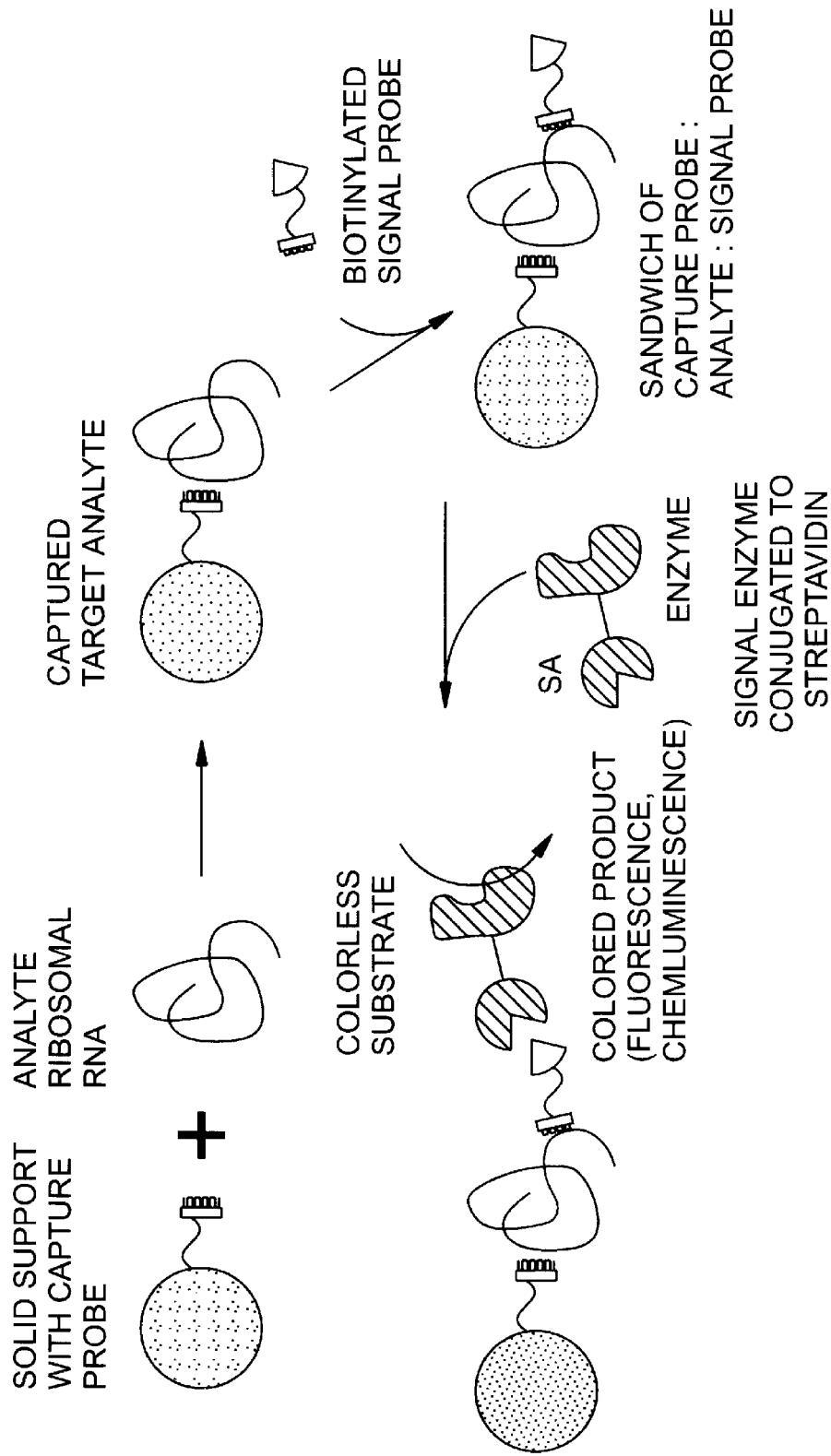

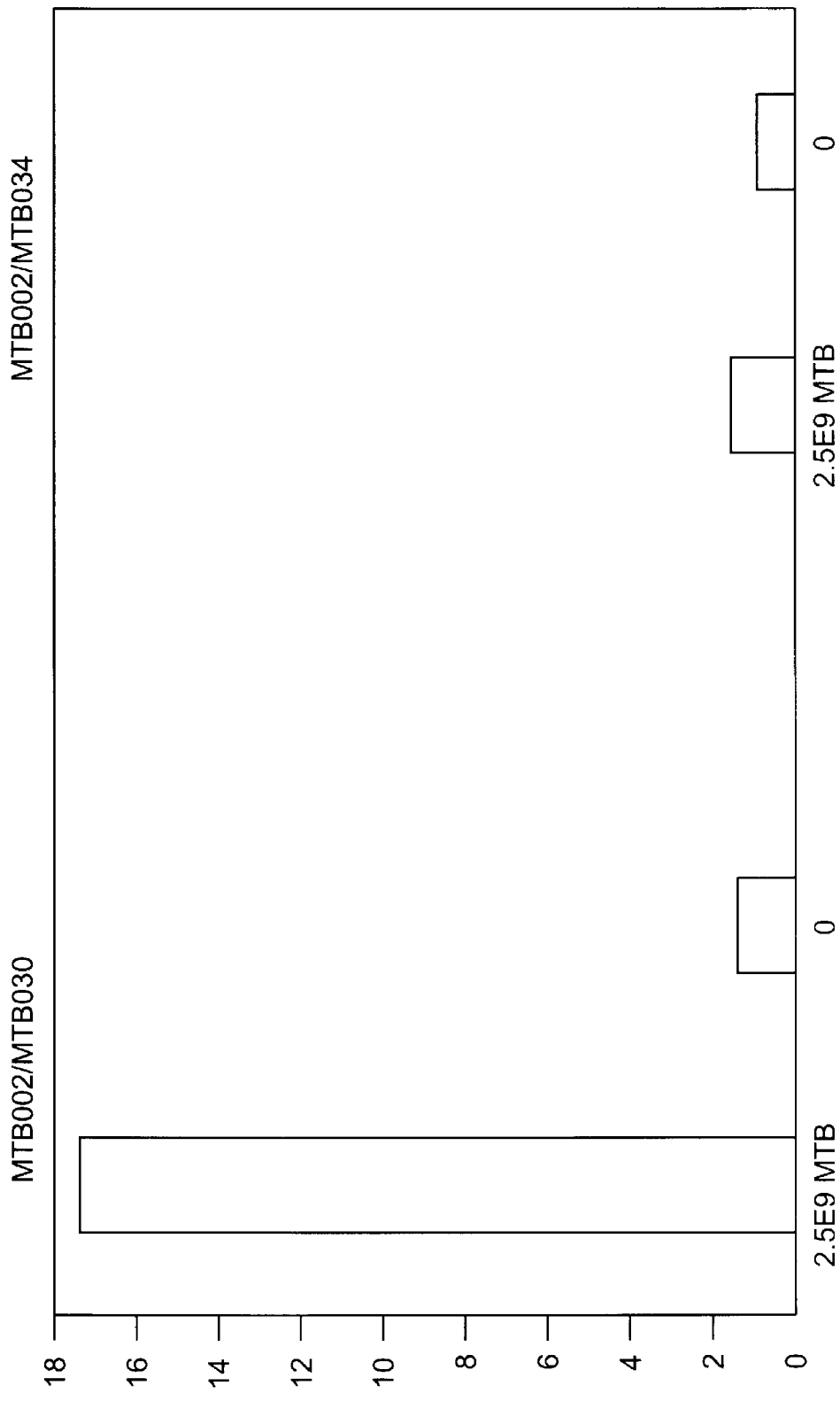

SEQUENCE LISTING ( 1 ) GENERAL INFORMATION:

( i i i ) NUMBER OF SEQUENCES: 89

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Mycobacterium tuberculosis ( i x ) FEATURE:
        ( A ) NAME/KEY: precursor_RNA
        ( B ) LOCATION: 1..25
        ( D ) OTHER INFORMATION: /note= "pre-16S rRNA open region target
            sequence complementary to probe MTB027"

( x i ) SEQUENCE DESCRIPTION: SEQ ID NO:1:

A A G G A G C A C C     A G C A A A A C G C     C C C C C                                                    2 5

( 2 ) INFORMATION FOR SEQ ID NO:2:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: rRNA ( v i ) ORIGINAL SOURCE:
  ( A ) ORGANISM: Mycobacterium tuberculosis ( i x ) FEATURE:
  ( A ) NAME/KEY: precursor_RNA
  ( B ) LOCATION: 1..25
  ( D ) OTHER INFORMATION: /note= "pre-16S rRNA open region target sequence complementary to probe MTB035"

( x i ) SEQUENCE DESCRIPTION: SEQ ID NO:2:

GGGUGCAUGA CAACAAAGUU GGCCA 25

( 2 ) INFORMATION FOR SEQ ID NO:3:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: rRNA ( v i ) ORIGINAL SOURCE:
  ( A ) ORGANISM: Mycobacterium tuberculosis ( i x ) FEATURE:
  ( A ) NAME/KEY: precursor_RNA
  ( B ) LOCATION: 1..30
  ( D ) OTHER INFORMATION: /note= "pre-16S rRNA open region target sequence complementary to probe MTB024"

( x i ) SEQUENCE DESCRIPTION: SEQ ID NO:3:

GGCCACCACC ACACUGUUGG GUCCUGAGGC 30

( 2 ) INFORMATION FOR SEQ ID NO:4:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: rRNA ( v i ) ORIGINAL SOURCE:
  ( A ) ORGANISM: Mycobacterium tuberculosis ( i x ) FEATURE:
  ( A ) NAME/KEY: precursor_RNA
  ( B ) LOCATION: 1..26
  ( D ) OTHER INFORMATION: /note= "pre-23S rRNA open region target sequence complementary to probe MTB017"

( x i ) SEQUENCE DESCRIPTION: SEQ ID NO:4:

UUGCGAGCAU CAAUGGAUAC GCUGCC 26

( 2 ) INFORMATION FOR SEQ ID NO:5:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: rRNA (v i) ORIGINAL SOURCE:
     (A) ORGANISM: Mycobacterium tuberculosis (i x) FEATURE:
     (A) NAME/KEY: precursor_RNA
     (B) LOCATION: 1..24
     (D) OTHER INFORMATION: /note= "pre-23S rRNA open region target sequence complementary to probe MTB016"

(x i) SEQUENCE DESCRIPTION: SEQ ID NO:5:

ACGCUGCCGG CUAGCGGUGG CGUG                                                     24

(2) INFORMATION FOR SEQ ID NO:6:

(i) SEQUENCE CHARACTERISTICS:
     (A) LENGTH: 33 base pairs
     (B) TYPE: nucleic acid
     (C) STRANDEDNESS: single
     (D) TOPOLOGY: linear (i i) MOLECULE TYPE: rRNA (v i) ORIGINAL SOURCE:
     (A) ORGANISM: Mycobacterium tuberculosis (i x) FEATURE:
     (A) NAME/KEY: precursor_RNA
     (B) LOCATION: 1..33
     (D) OTHER INFORMATION: /note= "pre-23S rRNA open region target sequence complementary to probe MTB015"

(x i) SEQUENCE DESCRIPTION: SEQ ID NO:6:

UUCUUUGUGC AAUAUUCUUU GGUUUUUGUU GUG                                           33

(2) INFORMATION FOR SEQ ID NO:7:

(i) SEQUENCE CHARACTERISTICS:
     (A) LENGTH: 23 base pairs
     (B) TYPE: nucleic acid
     (C) STRANDEDNESS: single
     (D) TOPOLOGY: linear (i i) MOLECULE TYPE: rRNA (v i) ORIGINAL SOURCE:
     (A) ORGANISM: Mycobacterium tuberculosis (i x) FEATURE:
     (A) NAME/KEY: precursor_RNA
     (B) LOCATION: 1..23
     (D) OTHER INFORMATION: /note= "pre-16S rRNA open region target sequence complementary to probe MTB018"

(x i) SEQUENCE DESCRIPTION: SEQ ID NO:7:

UUGUCGGGGG GCGUGGCCGU UUG                                                      23

(2) INFORMATION FOR SEQ ID NO:8:

(i) SEQUENCE CHARACTERISTICS:
     (A) LENGTH: 25 base pairs
     (B) TYPE: nucleic acid
     (C) STRANDEDNESS: single
     (D) TOPOLOGY: linear (i i) MOLECULE TYPE: rRNA (v i) ORIGINAL SOURCE:
     (A) ORGANISM: Mycobacterium bovis (i x) FEATURE:
     (A) NAME/KEY: precursor_RNA
     (B) LOCATION: 1..25
     (D) OTHER INFORMATION: /note= "pre-16S rRNA open region target sequence complementary to probe MTB030"

( x i ) SEQUENCE DESCRIPTION: SEQ ID NO:8:

CCCUUUUCCA AAGGGAGUGU UUGGG                                      25

( 2 ) INFORMATION FOR SEQ ID NO:9:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Mycobacterium bovis ( i x ) FEATURE:
        ( A ) NAME/KEY: precursor_RNA
        ( B ) LOCATION: 1..23
        ( D ) OTHER INFORMATION: /note= "pre-rRNA open region"

( x i ) SEQUENCE DESCRIPTION: SEQ ID NO:9:

AAGGAGCACC ACGAAAACGC CCC 23

( 2 ) INFORMATION FOR SEQ ID NO:10:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Mycobacterium bovis ( i x ) FEATURE:
( A ) NAME/KEY: precursor_RNA
( B ) LOCATION: 1..23
( D ) OTHER INFORMATION: /note= "pre-16s rRNA open region target sequence complementary to probe MTB027"

( x i ) SEQUENCE DESCRIPTION: SEQ ID NO:10:

AAGGAGCACC AGCAAAACGC CCC 23

( 2 ) INFORMATION FOR SEQ ID NO:11:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Mycobacterium bovis ( i x ) FEATURE:
( A ) NAME/KEY: precursor_RNA
( B ) LOCATION: 1..16
( D ) OTHER INFORMATION: /note= "pre-rRNA open region"

( x i ) SEQUENCE DESCRIPTION: SEQ ID NO:11:

GGCUAGCGGU GGCGUG 16

( 2 ) INFORMATION FOR SEQ ID NO:12:

( i ) SEQUENCE CHARACTERISTICS:
( A ) LENGTH: 25 base pairs ( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Mycobacterium avium ( i x ) FEATURE:
( A ) NAME/KEY: precursor_RNA
( B ) LOCATION: 1..25
( D ) OTHER INFORMATION: /note= "pre-rRNA open region"

( x i ) SEQUENCE DESCRIPTION: SEQ ID NO:12:

AAGGAGCACC ACGAAAAGCA CCCCC 25

( 2 ) INFORMATION FOR SEQ ID NO:13:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Mycobacterium avium ( i x ) FEATURE:
( A ) NAME/KEY: precursor_RNA
( B ) LOCATION: 1..26
( D ) OTHER INFORMATION: /note= "pre-rRNA open region"

( x i ) SEQUENCE DESCRIPTION: SEQ ID NO:13:

GGGUGCGCAA CAGCAAAUGA UUGCCA 26

( 2 ) INFORMATION FOR SEQ ID NO:14:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Mycobacterium avium ( i x ) FEATURE:
( A ) NAME/KEY: precursor_RNA
( B ) LOCATION: 1..27
( D ) OTHER INFORMATION: /note= "pre-rRNA open region"

( x i ) SEQUENCE DESCRIPTION: SEQ ID NO:14:

GCCAGACACA CUAUUGGGCC CUGAGAC 27

( 2 ) INFORMATION FOR SEQ ID NO:15:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Mycobacterium avium ( i x ) FEATURE:
( A ) NAME/KEY: precursor_RNA ( B ) LOCATION: 1..27
( D ) OTHER INFORMATION: /note= "pre-rRNA open region"

( x i ) SEQUENCE DESCRIPTION: SEQ ID NO:15:

UUGCGAGCAU CUAGAUGAGC GCAUGGU                                                    27

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Mycobacterium avium ( i x ) FEATURE:
        ( A ) NAME/KEY: precursor_RNA
        ( B ) LOCATION: 1..25
        ( D ) OTHER INFORMATION: /note= "pre-rRNA open region"

( x i ) SEQUENCE DESCRIPTION: SEQ ID NO:16:

CGCAUGGUCU UCGUGGCCGG CGUUC                                                      25

( 2 ) INFORMATION FOR SEQ ID NO:17:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Mycobacterium avium ( i x ) FEATURE:
        ( A ) NAME/KEY: precursor_RNA
        ( B ) LOCATION: 1..34
        ( D ) OTHER INFORMATION: /note= "pre-rRNA open region"

( x i ) SEQUENCE DESCRIPTION: SEQ ID NO:17:

AUCGAAAUGU GUAAUUUCUU UUUUAACUCU UGUG                                            34

( 2 ) INFORMATION FOR SEQ ID NO:18:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Mycobacterium avium ( i x ) FEATURE:
        ( A ) NAME/KEY: precursor_RNA
        ( B ) LOCATION: 1..16
        ( D ) OTHER INFORMATION: /note= "pre-rRNA open region"

( x i ) SEQUENCE DESCRIPTION: SEQ ID NO:18:

UGUGUGGGUA UGGCAA                                                                16

( 2 ) INFORMATION FOR SEQ ID NO:19:

( i ) SEQUENCE CHARACTERISTICS:

(A) LENGTH: 35 base pairs
                (B) TYPE: nucleic acid
                (C) STRANDEDNESS: single
                (D) TOPOLOGY: linear (i i) MOLECULE TYPE: rRNA (v i) ORIGINAL SOURCE:
                (A) ORGANISM: Mycobacterium avium (i x) FEATURE:
                (A) NAME/KEY: precursor_RNA
                (B) LOCATION: 1..35
                (D) OTHER INFORMATION: /note= "pre-rRNA open region"

(x i) SEQUENCE DESCRIPTION: SEQ ID NO:19:

CUUGAUUUGA AAUUCACCUC GCUGCGCGAG GAGAU                    35

(2) INFORMATION FOR SEQ ID NO:20:

(i) SEQUENCE CHARACTERISTICS:
                (A) LENGTH: 24 base pairs
                (B) TYPE: nucleic acid
                (C) STRANDEDNESS: single
                (D) TOPOLOGY: linear (i i) MOLECULE TYPE: rRNA (v i) ORIGINAL SOURCE:
                (A) ORGANISM: Mycobacterium lufu (i x) FEATURE:
                (A) NAME/KEY: precursor_RNA
                (B) LOCATION: 1..24
                (D) OTHER INFORMATION: /note= "pre-rRNA open region"

(x i) SEQUENCE DESCRIPTION: SEQ ID NO:20:

AAGGAGCACC ACGAAAAGCU ACCC                                24

(2) INFORMATION FOR SEQ ID NO:21:

(i) SEQUENCE CHARACTERISTICS:
                (A) LENGTH: 26 base pairs
                (B) TYPE: nucleic acid
                (C) STRANDEDNESS: single
                (D) TOPOLOGY: linear (i i) MOLECULE TYPE: rRNA (v i) ORIGINAL SOURCE:
                (A) ORGANISM: Mycobacterium lufu (i x) FEATURE:
                (A) NAME/KEY: precursor_RNA
                (B) LOCATION: 1..26
                (D) OTHER INFORMATION: /note= "pre-rRNA open region"

(x i) SEQUENCE DESCRIPTION: SEQ ID NO:21:

GGGUGCACAA CAGCAAAUGA UUGCCA                              26

(2) INFORMATION FOR SEQ ID NO:22:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (i i) MOLECULE TYPE: rRNA (v i) ORIGINAL SOURCE:
                (A) ORGANISM: Mycobacterium lufu (i x) FEATURE:

( A ) NAME/KEY: precursor_RNA
( B ) LOCATION: 1..27
( D ) OTHER INFORMATION: /note= "pre-rRNA open region"

( x i ) SEQUENCE DESCRIPTION: SEQ ID NO:22:

UUGCGAGCUA CUAGAUGAAC GCGUAGU                    27

( 2 ) INFORMATION FOR SEQ ID NO:23:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Mycobacterium lufu ( i x ) FEATURE:
( A ) NAME/KEY: precursor_RNA
( B ) LOCATION: 1..27
( D ) OTHER INFORMATION: /note= "pre-rRNA open region"

( x i ) SEQUENCE DESCRIPTION: SEQ ID NO:23:

CGCGUAGUCC UUGGGGCUGA CGAGUUC                    27

( 2 ) INFORMATION FOR SEQ ID NO:24:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Mycobacterium lufu ( i x ) FEATURE:
( A ) NAME/KEY: precursor_RNA
( B ) LOCATION: 1..34
( D ) OTHER INFORMATION: /note= "pre-rRNA open region"

( x i ) SEQUENCE DESCRIPTION: SEQ ID NO:24:

AUCGAAAUGU GUUAUUUCUU UUUUAACUCU UGUG            34

( 2 ) INFORMATION FOR SEQ ID NO:25:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Mycobacterium lufu ( i x ) FEATURE:
( A ) NAME/KEY: precursor_RNA
( B ) LOCATION: 1..17
( D ) OTHER INFORMATION: /note= "pre-rRNA open region"

( x i ) SEQUENCE DESCRIPTION: SEQ ID NO:25:

UGUGUGGGUA UGGUUGU                               17

( 2 ) INFORMATION FOR SEQ ID NO:26:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Mycobacterium lufu ( i x ) FEATURE:
( A ) NAME/KEY: precursor_RNA
( B ) LOCATION: 1..33
( D ) OTHER INFORMATION: /note= "pre-rRNA open region"

( x i ) SEQUENCE DESCRIPTION: SEQ ID NO:26:

CUGAUUUGAA UUCACCUCGU UCUGCGAGGA GUU                33

( 2 ) INFORMATION FOR SEQ ID NO:27:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Mycobacterium intracellulare ( i x ) FEATURE:
( A ) NAME/KEY: precursor_RNA
( B ) LOCATION: 1..24
( D ) OTHER INFORMATION: /note= "pre-rRNA open region"

( x i ) SEQUENCE DESCRIPTION: SEQ ID NO:27:

AAGGAGCACC ACGAAAAGCA CUCC                         24

( 2 ) INFORMATION FOR SEQ ID NO:28:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Mycobacterium intracellulare ( i x ) FEATURE:
( A ) NAME/KEY: precursor_RNA
( B ) LOCATION: 1..27
( D ) OTHER INFORMATION: /note= "pre-rRNA open region"

( x i ) SEQUENCE DESCRIPTION: SEQ ID NO:28:

UUGCGAGCAU CUAGAUGAGC GCAUAGU                      27

( 2 ) INFORMATION FOR SEQ ID NO:29:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: rRNA ( v i ) ORIGINAL SOURCE:
( A ) ORGANISM: Mycobacterium intracellulare (ix) FEATURE:
 (A) NAME/KEY: precursor_RNA
 (B) LOCATION: 1..23
 (D) OTHER INFORMATION: /note= "pre-rRNA open region"

(xi) SEQUENCE DESCRIPTION: SEQ ID NO:29:

CGCAUAGUCC UUAGUGAUGC GUC    23

(2) INFORMATION FOR SEQ ID NO:30:

(i) SEQUENCE CHARACTERISTICS:
  (A) LENGTH: 34 base pairs
  (B) TYPE: nucleic acid
  (C) STRANDEDNESS: single
  (D) TOPOLOGY: linear (ii) MOLECULE TYPE: rRNA (vi) ORIGINAL SOURCE:
  (A) ORGANISM: Mycobacterium intracellulare (ix) FEATURE:
  (A) NAME/KEY: precursor_RNA
  (B) LOCATION: 1..34
  (D) OTHER INFORMATION: /note= "pre-rRNA open region"

(xi) SEQUENCE DESCRIPTION: SEQ ID NO:30:

GUCGAAAUGU GUAAUUUCUU CUUUGGUUUU UGUG    34

(2) INFORMATION FOR SEQ ID NO:31:

(i) SEQUENCE CHARACTERISTICS:
  (A) LENGTH: 34 base pairs
  (B) TYPE: nucleic acid
  (C) STRANDEDNESS: single
  (D) TOPOLOGY: linear (ii) MOLECULE TYPE: rRNA (vi) ORIGINAL SOURCE:
  (A) ORGANISM: Mycobacterium intracellulare (ix) FEATURE:
  (A) NAME/KEY: precursor_RNA
  (B) LOCATION: 1..34
  (D) OTHER INFORMATION: /note= "pre-rRNA open region"

(xi) SEQUENCE DESCRIPTION: SEQ ID NO:31:

CUGAUUUGAA AUUCACCUCG UUCAUCGAGG AGUU    34

(2) INFORMATION FOR SEQ ID NO:32:

(i) SEQUENCE CHARACTERISTICS:
  (A) LENGTH: 26 base pairs
  (B) TYPE: nucleic acid
  (C) STRANDEDNESS: single
  (D) TOPOLOGY: linear (ii) MOLECULE TYPE: rRNA (vi) ORIGINAL SOURCE:
  (A) ORGANISM: Mycobacterium leprae (ix) FEATURE:
  (A) NAME/KEY: precursor_RNA
  (B) LOCATION: 1..26
  (D) OTHER INFORMATION: /note= "pre-rRNA open region"

(xi) SEQUENCE DESCRIPTION: SEQ ID NO:32:

AAGGAGCACC ACGAAAAACA CUCUAA    26

(2) INFORMATION FOR SEQ ID NO:33:

(i) SEQUENCE CHARACTERISTICS:
   (A) LENGTH: 23 base pairs
   (B) TYPE: nucleic acid
   (C) STRANDEDNESS: single
   (D) TOPOLOGY: linear (ii) MOLECULE TYPE: rRNA (vi) ORIGINAL SOURCE:
   (A) ORGANISM: Mycobacterium leprae (ix) FEATURE:
   (A) NAME/KEY: precursor_RNA
   (B) LOCATION: 1..23
   (D) OTHER INFORMATION: /note= "pre-rRNA open region"

(xi) SEQUENCE DESCRIPTION: SEQ ID NO:33:

GGGUGCGCAA CAGCAAAUAU CCA                      23

(2) INFORMATION FOR SEQ ID NO:34:

(i) SEQUENCE CHARACTERISTICS:
   (A) LENGTH: 26 base pairs
   (B) TYPE: nucleic acid
   (C) STRANDEDNESS: single
   (D) TOPOLOGY: linear (ii) MOLECULE TYPE: rRNA (vi) ORIGINAL SOURCE:
   (A) ORGANISM: Mycobacterium leprae (ix) FEATURE:
   (A) NAME/KEY: precursor_RNA
   (B) LOCATION: 1..26
   (D) OTHER INFORMATION: /note= "pre-rRNA open region"

(xi) SEQUENCE DESCRIPTION: SEQ ID NO:34:

CCAGACACAC UGUUGGGUCC UGAGGC                   26

(2) INFORMATION FOR SEQ ID NO:35:

(i) SEQUENCE CHARACTERISTICS:
   (A) LENGTH: 28 base pairs
   (B) TYPE: nucleic acid
   (C) STRANDEDNESS: single
   (D) TOPOLOGY: linear (ii) MOLECULE TYPE: rRNA (vi) ORIGINAL SOURCE:
   (A) ORGANISM: Mycobacterium leprae (ix) FEATURE:
   (A) NAME/KEY: precursor_RNA
   (B) LOCATION: 1..28
   (D) OTHER INFORMATION: /note= "pre-rRNA open region"

(xi) SEQUENCE DESCRIPTION: SEQ ID NO:35:

UUGCGAGCAU CUAAAUGGAU GCGUUGUC                 28

(2) INFORMATION FOR SEQ ID NO:36:

(i) SEQUENCE CHARACTERISTICS:
   (A) LENGTH: 27 base pairs
   (B) TYPE: nucleic acid
   (C) STRANDEDNESS: single
   (D) TOPOLOGY: linear (ii) MOLECULE TYPE: rRNA (vi) ORIGINAL SOURCE:
   (A) ORGANISM: Mycobacterium leprae ( i x ) FEATURE:
    ( A ) NAME/KEY: precursor_RNA
    ( B ) LOCATION: 1..27
    ( D ) OTHER INFORMATION: /note= "pre-rRNA open region"

( x i ) SEQUENCE DESCRIPTION: SEQ ID NO:36:

GCGUUGUCAG UUAUGUAGUG GUGGCGU 27

( 2 ) INFORMATION FOR SEQ ID NO:37:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Mycobacterium leprae ( i x ) FEATURE:
        ( A ) NAME/KEY: precursor_RNA
        ( B ) LOCATION: 1..39
        ( D ) OTHER INFORMATION: /note= "pre-rRNA open region"

( x i ) SEQUENCE DESCRIPTION: SEQ ID NO:37:

AUUCAUUGAA AAUGUGUAAU UUUCUUCUUU GGUUUUGUG 39

( 2 ) INFORMATION FOR SEQ ID NO:38:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Mycobacterium leprae ( i x ) FEATURE:
        ( A ) NAME/KEY: precursor_RNA
        ( B ) LOCATION: 1..22
        ( D ) OTHER INFORMATION: /note= "pre-rRNA open region"

( x i ) SEQUENCE DESCRIPTION: SEQ ID NO:38:

UGUGUGUAGG UGUAGUUUAU UA 22

( 2 ) INFORMATION FOR SEQ ID NO:39:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Mycobacterium leprae ( i x ) FEATURE:
        ( A ) NAME/KEY: precursor_RNA
        ( B ) LOCATION: 1..38
        ( D ) OTHER INFORMATION: /note= "pre-rRNA open region"

( x i ) SEQUENCE DESCRIPTION: SEQ ID NO:39:

CUAGAAAUUG AAAAUUUCGU CUAGUUAUUG AUGGAGUU 38

( 2 ) INFORMATION FOR SEQ ID NO:40:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Mycobacterium paratuberculosis ( i x ) FEATURE:
        ( A ) NAME/KEY: precursor_RNA
        ( B ) LOCATION: 1..34
        ( D ) OTHER INFORMATION: /note= "pre-rRNA open region"

( x i ) SEQUENCE DESCRIPTION: SEQ ID NO:40:

CUGAUUUGAA AUUCACCUCG CUGCGCGAGG AGAU        34

( 2 ) INFORMATION FOR SEQ ID NO:41:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Mycobacterium marinum ( i x ) FEATURE:
        ( A ) NAME/KEY: precursor_RNA
        ( B ) LOCATION: 1..18
        ( D ) OTHER INFORMATION: /note= "pre-rRNA open region"

( x i ) SEQUENCE DESCRIPTION: SEQ ID NO:41:

UGUGAGGGAG UAGUCGUU        18

( 2 ) INFORMATION FOR SEQ ID NO:42:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:
        ( A ) ORGANISM: Mycobacterium marinum ( i x ) FEATURE:
        ( A ) NAME/KEY: precursor_RNA
        ( B ) LOCATION: 1..33
        ( D ) OTHER INFORMATION: /note= "pre-rRNA open region"

( x i ) SEQUENCE DESCRIPTION: SEQ ID NO:42:

CUGAUUGCGA AUUCACCUCG UUAUCGAGGG GUU        33

( 2 ) INFORMATION FOR SEQ ID NO:43:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: rRNA ( v i ) ORIGINAL SOURCE:

(A) ORGANISM: Mycobacterium habana (ix) FEATURE:
(A) NAME/KEY: precursor_RNA
(B) LOCATION: 1..17
(D) OTHER INFORMATION: /note= "pre-rRNA open region"

(xi) SEQUENCE DESCRIPTION: SEQ ID NO:43:

UGUGUAGGUA UGGUCGU 17

(2) INFORMATION FOR SEQ ID NO:44:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: rRNA (vi) ORIGINAL SOURCE:
(A) ORGANISM: Mycobacterium habana (ix) FEATURE:
(A) NAME/KEY: precursor_RNA
(B) LOCATION: 1..43
(D) OTHER INFORMATION: /note= "pre-rRNA open region"

(xi) SEQUENCE DESCRIPTION: SEQ ID NO:44:

CAGAUUAUCU CUGAUUCGAA UCCACCUCGU UGAUCGAGGA GAU 43

(2) INFORMATION FOR SEQ ID NO:45:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: rRNA (vi) ORIGINAL SOURCE:
(A) ORGANISM: Mycobacterium habana (ix) FEATURE:
(A) NAME/KEY: precursor_RNA
(B) LOCATION: 1..24
(D) OTHER INFORMATION: /note= "pre-rRNA open region"

(xi) SEQUENCE DESCRIPTION: SEQ ID NO:45:

AAGGAGCACC ACGAGAAACA CUCC 24

(2) INFORMATION FOR SEQ ID NO:46:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: rRNA (vi) ORIGINAL SOURCE:
(A) ORGANISM: Mycobacterium habana (ix) FEATURE:
(A) NAME/KEY: precursor_RNA
(B) LOCATION: 1..26
(D) OTHER INFORMATION: /note= "pre-rRNA open region"

(xi) SEQUENCE DESCRIPTION: SEQ ID NO:46:

GGGUGCACAA CAACAGGCAA UCGCCA 26

( 2 ) INFORMATION FOR SEQ ID NO:47:

( i ) SEQUENCE CHARACTERISTICS:
           ( A ) LENGTH: 29 base pairs
           ( B ) TYPE: nucleic acid
           ( C ) STRANDEDNESS: unknown
           ( D ) TOPOLOGY: unknown ( i i ) MOLECULE TYPE: rRNA ( v i ) ORIGINAL SOURCE:
           ( A ) ORGANISM: Mycobacterium tuberculosis ( i x ) FEATURE:
           ( A ) NAME/KEY: rRNA
           ( B ) LOCATION: 1..29
           ( D ) OTHER INFORMATION: /note= "mature rRNA open region
                target sequence complementary to
                probe MTB001"

( x i ) SEQUENCE DESCRIPTION: SEQ ID NO:47:

CCAGUGGCCU AACCCUCGGG AGGGAGCUG                                                      29

( 2 ) INFORMATION FOR SEQ ID NO:48:

( i ) SEQUENCE CHARACTERISTICS:
           ( A ) LENGTH: 27 base pairs
           ( B ) TYPE: nucleic acid
           ( C ) STRANDEDNESS: unknown
           ( D ) TOPOLOGY: unknown ( i i ) MOLECULE TYPE: rRNA ( v i ) ORIGINAL SOURCE:
           ( A ) ORGANISM: Mycobacterium tuberculosis ( i x ) FEATURE:
           ( A ) NAME/KEY: rRNA
           ( B ) LOCATION: 1..27
           ( D ) OTHER INFORMATION: /note= "mature rRNA open region
                target sequence complementary to
                probe MTB002"

( x i ) SEQUENCE DESCRIPTION: SEQ ID NO:48:

CGAACGGAAA GGUCUCUUCG GAGAUAC                                                       27

( 2 ) INFORMATION FOR SEQ ID NO:49:

( i ) SEQUENCE CHARACTERISTICS:
           ( A ) LENGTH: 28 base pairs
           ( B ) TYPE: nucleic acid
           ( C ) STRANDEDNESS: unknown
           ( D ) TOPOLOGY: unknown ( i i ) MOLECULE TYPE: rRNA ( v i ) ORIGINAL SOURCE:
           ( A ) ORGANISM: Mycobacterium tuberculosis ( i x ) FEATURE:
           ( A ) NAME/KEY: rRNA
           ( B ) LOCATION: 1..28
           ( D ) OTHER INFORMATION: /note= "mature rRNA open region
                target sequence complementary to
                probe MTB004"

( x i ) SEQUENCE DESCRIPTION: SEQ ID NO:49:

AGGUCCGGGU UCUCUCGGAU UGACGGUA                                                   28

( 2 ) INFORMATION FOR SEQ ID NO:50:

( i ) SEQUENCE CHARACTERISTICS:
           ( A ) LENGTH: 26 base pairs (B) TYPE: nucleic acid
(C) STRANDEDNESS: unknown
(D) TOPOLOGY: unknown (i i) MOLECULE TYPE: rRNA (v i) ORIGINAL SOURCE:
(A) ORGANISM: Mycobacterium bovis (x i) SEQUENCE DESCRIPTION: SEQ ID NO:50:

CGAACGGAAA GGUCUCUUCG GAGAUA                26

(2) INFORMATION FOR SEQ ID NO:51:

(i) SEQUENCE CHARACTERISTICS:
(A) LENGTH: 27 base pairs
(B) TYPE: nucleic acid
(C) STRANDEDNESS: unknown
(D) TOPOLOGY: unknown (i i) MOLECULE TYPE: rRNA (v i) ORIGINAL SOURCE:
(A) ORGANISM: Mycobacterium bovis (x i) SEQUENCE DESCRIPTION: SEQ ID NO:51:

AGGUCCGGGU UCUCUCGGAU UGACGGU              27

(2) INFORMATION FOR SEQ ID NO:52:

(i) SEQUENCE CHARACTERISTICS:
(A) LENGTH: 31 base pairs
(B) TYPE: nucleic acid
(C) STRANDEDNESS: unknown
(D) TOPOLOGY: unknown (i i) MOLECULE TYPE: rRNA (v i) ORIGINAL SOURCE:
(A) ORGANISM: Mycobacterium avium (x i) SEQUENCE DESCRIPTION: SEQ ID NO:52:

CCAGUGGCCU AACCCUUUUG GGAGGGAGCU G         31

(2) INFORMATION FOR SEQ ID NO:53:

(i) SEQUENCE CHARACTERISTICS:
(A) LENGTH: 27 base pairs
(B) TYPE: nucleic acid
(C) STRANDEDNESS: unknown
(D) TOPOLOGY: unknown (i i) MOLECULE TYPE: rRNA (v i) ORIGINAL SOURCE:
(A) ORGANISM: Mycobacterium avium (x i) SEQUENCE DESCRIPTION: SEQ ID NO:53:

CGAACGGAAA GGCCUCUUCG GAGGUAC              27

(2) INFORMATION FOR SEQ ID NO:54:

(i) SEQUENCE CHARACTERISTICS:
(A) LENGTH: 28 base pairs
(B) TYPE: nucleic acid
(C) STRANDEDNESS: unknown
(D) TOPOLOGY: unknown (i i) MOLECULE TYPE: rRNA (v i) ORIGINAL SOURCE:
(A) ORGANISM: Mycobacterium avium ( x i ) SEQUENCE DESCRIPTION: SEQ ID NO:54:

AGGUCCGGGU UUUCUCGGAU UGACGGUA                                                                28

( 2 ) INFORMATION FOR SEQ ID NO:55:

( i ) SEQUENCE CHARACTERISTICS:
        ( A ) LENGTH: 29 base pairs
        ( B ) TYPE: nucleic acid
        ( C ) STRANDEDNESS: unknown
        ( D ) TOPOLOGY: unknown ( i i ) MOLECULE TYPE: rRNA ( v i ) ORIGINAL SOURCE:
        ( A ) ORGANISM: Mycobacterium intracellulare ( x i ) SEQUENCE DESCRIPTION: SEQ ID NO:55:

CCAGUGGCCU AACCCUUGGG AGGGAGCUG                                                               29

( 2 ) INFORMATION FOR SEQ ID NO:56:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: rRNA ( v i ) ORIGINAL SOURCE:
        ( A ) ORGANISM: Mycobacterium intracellulare ( x i ) SEQUENCE DESCRIPTION: SEQ ID NO:56:

GAACGGAAAG NCCCUUCGGG UAC                                                                     23

( 2 ) INFORMATION FOR SEQ ID NO:57:

( i ) SEQUENCE CHARACTERISTICS:
        ( A ) LENGTH: 35 base pairs
        ( B ) TYPE: nucleic acid
        ( C ) STRANDEDNESS: unknown
        ( D ) TOPOLOGY: unknown ( i i ) MOLECULE TYPE: rRNA ( v i ) ORIGINAL SOURCE:
        ( A ) ORGANISM: Mycobacterium intracellulare ( x i ) SEQUENCE DESCRIPTION: SEQ ID NO:57:

AGGUCCGGGG GGGGGGUUUU CUCGGAUUGA CGGUA                                                         35

( 2 ) INFORMATION FOR SEQ ID NO:58:

( i ) SEQUENCE CHARACTERISTICS:
        ( A ) LENGTH: 39 base pairs
        ( B ) TYPE: nucleic acid
        ( C ) STRANDEDNESS: unknown
        ( D ) TOPOLOGY: unknown ( i i ) MOLECULE TYPE: rRNA ( v i ) ORIGINAL SOURCE:
        ( A ) ORGANISM: Mycobacterium leprae ( x i ) SEQUENCE DESCRIPTION: SEQ ID NO:58:

CGAACGGAAA GGUCUCUAAA AAAUCUUUUU UAGAGAUAC                                                     39

( 2 ) INFORMATION FOR SEQ ID NO:59:

( i ) SEQUENCE CHARACTERISTICS:
    ( A ) LENGTH: 36 base pairs
    ( B ) TYPE: nucleic acid
    ( C ) STRANDEDNESS: unknown
    ( D ) TOPOLOGY: unknown ( i i ) MOLECULE TYPE: rRNA ( v i ) ORIGINAL SOURCE:
    ( A ) ORGANISM: Mycobacterium leprae ( x i ) SEQUENCE DESCRIPTION: SEQ ID NO:59:

AGGUCUGGGG GGGGGGGUUU UCUCGGAUUG ACGGUA 36

( 2 ) INFORMATION FOR SEQ ID NO:60:

( i ) SEQUENCE CHARACTERISTICS:
    ( A ) LENGTH: 29 base pairs
    ( B ) TYPE: nucleic acid
    ( C ) STRANDEDNESS: unknown
    ( D ) TOPOLOGY: unknown ( i i ) MOLECULE TYPE: rRNA ( v i ) ORIGINAL SOURCE:
    ( A ) ORGANISM: Mycobacterium habana ( x i ) SEQUENCE DESCRIPTION: SEQ ID NO:60:

CCAGUGGCCU AACCUUUUGG AGGGAGCUG 29

( 2 ) INFORMATION FOR SEQ ID NO:61:

( i ) SEQUENCE CHARACTERISTICS:
    ( A ) LENGTH: 25 base pairs
    ( B ) TYPE: nucleic acid
    ( C ) STRANDEDNESS: unknown
    ( D ) TOPOLOGY: unknown ( i i ) MOLECULE TYPE: rRNA ( v i ) ORIGINAL SOURCE:
    ( A ) ORGANISM: Mycobacterium habana ( x i ) SEQUENCE DESCRIPTION: SEQ ID NO:61:

CGAACGGAAA GNCCCUUCGG GNUAC 25

( 2 ) INFORMATION FOR SEQ ID NO:62:

( i ) SEQUENCE CHARACTERISTICS:
    ( A ) LENGTH: 16 base pairs
    ( B ) TYPE: nucleic acid
    ( C ) STRANDEDNESS: unknown
    ( D ) TOPOLOGY: unknown ( i i ) MOLECULE TYPE: rRNA ( v i ) ORIGINAL SOURCE:
    ( A ) ORGANISM: Mycobacterium habana ( x i ) SEQUENCE DESCRIPTION: SEQ ID NO:62:

AGCGCAAGUG ACGGUA 16

( 2 ) INFORMATION FOR SEQ ID NO:63:

( i ) SEQUENCE CHARACTERISTICS:
    ( A ) LENGTH: 31 base pairs
    ( B ) TYPE: nucleic acid
    ( C ) STRANDEDNESS: unknown
    ( D ) TOPOLOGY: unknown ( i i ) MOLECULE TYPE: rRNA ( v i ) ORIGINAL SOURCE:
        ( A ) ORGANISM: Mycobacterium paratuberculosis ( x i ) SEQUENCE DESCRIPTION: SEQ ID NO:63:

CCAGUGGCCU AACCCUUUUG GCAGGGAGCU G                  31

( 2 ) INFORMATION FOR SEQ ID NO:64:

( i ) SEQUENCE CHARACTERISTICS:
        ( A ) LENGTH: 32 base pairs
        ( B ) TYPE: nucleic acid
        ( C ) STRANDEDNESS: unknown
        ( D ) TOPOLOGY: unknown ( i i ) MOLECULE TYPE: rRNA ( v i ) ORIGINAL SOURCE:
        ( A ) ORGANISM: Mycobacterium paratuberculosis ( x i ) SEQUENCE DESCRIPTION: SEQ ID NO:64:

CGAACGGGGG GGAAAGGCCU CUUCGGAGGU AC                 32

( 2 ) INFORMATION FOR SEQ ID NO:65:

( i ) SEQUENCE CHARACTERISTICS:
        ( A ) LENGTH: 29 base pairs
        ( B ) TYPE: nucleic acid
        ( C ) STRANDEDNESS: unknown
        ( D ) TOPOLOGY: unknown ( i i ) MOLECULE TYPE: rRNA ( v i ) ORIGINAL SOURCE:
        ( A ) ORGANISM: Mycobacterium marinum ( x i ) SEQUENCE DESCRIPTION: SEQ ID NO:65:

CCAGUGGCCU AACCUUUGGG AGGGAGCUG                    29

( 2 ) INFORMATION FOR SEQ ID NO:66:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: unknown ( i i ) MOLECULE TYPE: rRNA ( v i ) ORIGINAL SOURCE:
        ( A ) ORGANISM: Mycobacterium marinum ( x i ) SEQUENCE DESCRIPTION: SEQ ID NO:66:

AGGUUCGGGU UUUCUCGGAU UGACGGUA                     28

( 2 ) INFORMATION FOR SEQ ID NO:67:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Escherichia coli
        ( B ) STRAIN: ATCC 11775

( i x ) FEATURE:
        ( A ) NAME/KEY: misc_feature
        ( B ) LOCATION: 1..30
        ( D ) OTHER INFORMATION: /note= "probe EC012 complementary to pre-16S rRNA open region target
sequence +3 to +31 residues downstream
of mature 16S rRNA 3'terminus"

( x i ) SEQUENCE DESCRIPTION: SEQ ID NO:67:

GTGTGAGCAC TACAAAGTAC GCTTCTTTAA 30

( 2 ) INFORMATION FOR SEQ ID NO:68:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Escherichia coli
        ( B ) STRAIN: ATCC 11775

( i x ) FEATURE:
        ( A ) NAME/KEY: misc_feature
        ( B ) LOCATION: 1..30
        ( D ) OTHER INFORMATION: /note= "probe EC013 complementary
        to pre-16S rRNA open region target
        sequence spanning mature 16S rRNA 3'
        terminus from residue 1538 of mature
        16S rRNA to residue +25 downstream of
        mature 16S rRNA 3'terminus"

( x i ) SEQUENCE DESCRIPTION: SEQ ID NO:68:

GCACTACAAA GTACGCTTCT TTAAGGTAAG 30

( 2 ) INFORMATION FOR SEQ ID NO:69:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Escherichia coli
        ( B ) STRAIN: ATCC 11775

( i x ) FEATURE:
        ( A ) NAME/KEY: misc_feature
        ( B ) LOCATION: 1..29
        ( D ) OTHER INFORMATION: /note= "probe EC014 complementary
        to pre-16S rRNA open region target
        sequence - 102 to -73 residues upstream
        of mature 16S rRNA 5'terminus"

( x i ) SEQUENCE DESCRIPTION: SEQ ID NO:69:

ACTTGGTATT CATTTTTCGT CTTGCGACG 29

( 2 ) INFORMATION FOR SEQ ID NO:70:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Escherichia coli
        ( B ) STRAIN: ATCC 11775

( i x ) FEATURE:

(A) NAME/KEY: misc_feature
(B) LOCATION: 1..30
(D) OTHER INFORMATION: /note= "probe EC016 complementary to mature 16S rRNA open region target sequence residues 456 to 475"

(xi) SEQUENCE DESCRIPTION: SEQ ID NO:70:

GCAAAGGTAT TAACTTTACT CCCTTCCTCC        30

(2) INFORMATION FOR SEQ ID NO:71:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Escherichia coli
(B) STRAIN: ATCC 11775

(ix) FEATURE:
(A) NAME/KEY: misc_feature
(B) LOCATION: 1..28
(D) OTHER INFORMATION: /note= "probe EC020 complementary to mature 16S rRNA open region target sequence residues 179 to 206"

(xi) SEQUENCE DESCRIPTION: SEQ ID NO:71:

GTCCCCCTCT TTGGTCTTGC GACGTTAT        28

(2) INFORMATION FOR SEQ ID NO:72:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Escherichia coli
(B) STRAIN: ATCC 11775

(ix) FEATURE:
(A) NAME/KEY: misc_feature
(B) LOCATION: 1..19
(D) OTHER INFORMATION: /note= "probe UP042 complementary to mature 16S rRNA open region target sequence residues 1390 to 1409"

(xi) SEQUENCE DESCRIPTION: SEQ ID NO:72:

TGACGGGCGG TGTGTACAA        19

(2) INFORMATION FOR SEQ ID NO:73:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: Mycobacterium tuberculosis (ix) FEATURE:
(A) NAME/KEY: misc_feature
(B) LOCATION: 1..25
(D) OTHER INFORMATION: /note= "probe MTB030 complementary to pre-16S rRNA open region target
sequence from residue -1 upstream of
the mature 16S rRNA 5'terminus to
residue 24 of the mature 16S rRNA"

( x i ) SEQUENCE DESCRIPTION: SEQ ID NO:73:

CCCAAACACT CCCTTTGGAA AAGGG 25

( 2 ) INFORMATION FOR SEQ ID NO:74:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Mycobacterium tuberculosis ( i x ) FEATURE:
( A ) NAME/KEY: misc_feature
( B ) LOCATION: 1..27
( D ) OTHER INFORMATION: /note= "probe MTB002 complementary
to mature 16S rRNA open region target
sequence"

( x i ) SEQUENCE DESCRIPTION: SEQ ID NO:74:

GTATCTCCGA AGAGACCTTT CCGTTCG 27

( 2 ) INFORMATION FOR SEQ ID NO:75:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Mycobacterium tuberculosis ( i x ) FEATURE:
( A ) NAME/KEY: misc_feature
( B ) LOCATION: 1..30
( D ) OTHER INFORMATION: /note= "probe MTB034 complementary
to pre-16S rRNA open region target
sequence -96 to -67 residues upstream
of the mature 16S rRNA 5'terminus"

( x i ) SEQUENCE DESCRIPTION: SEQ ID NO:75:

GGCCAAAAAT AACAACAAAA ATGTGAAACC 30

( 2 ) INFORMATION FOR SEQ ID NO:76:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Mycobacterium smegmatis ( i x ) FEATURE:
( A ) NAME/KEY: misc_feature
( B ) LOCATION: 1..28
( D ) OTHER INFORMATION: /note= "probe MSM001 complementary
to mature rRNA open region target
sequence"

( x i ) SEQUENCE DESCRIPTION: SEQ ID NO:76:

CGGCTCCCTC CACAAGGGTT AGGCCACC 28

( 2 ) INFORMATION FOR SEQ ID NO:77:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium smegmatis ( i x ) FEATURE:
        ( A ) NAME/KEY: misc_feature
        ( B ) LOCATION: 1..19
        ( D ) OTHER INFORMATION: /note= "probe MSM008 complementary to pre-16S rRNA open region target sequence"

( x i ) SEQUENCE DESCRIPTION: SEQ ID NO:77:

TCACACCCTC CCCAACGGA 19

( 2 ) INFORMATION FOR SEQ ID NO:78:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium tuberculosis ( i x ) FEATURE:
        ( A ) NAME/KEY: misc_feature
        ( B ) LOCATION: 1..33
        ( D ) OTHER INFORMATION: /note= "probe MTB015 complementary to pre-23S rRNA open region target sequence from residue -1 upstream of the mature 23S rRNA 5'terminus to residue 32 of the mature 23S rRNA"

( x i ) SEQUENCE DESCRIPTION: SEQ ID NO:78:

CACAACAAAA ACCAAAGAAT ATTGCACAAA GAA 33

( 2 ) INFORMATION FOR SEQ ID NO:79:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium tuberculosis ( i x ) FEATURE:
        ( A ) NAME/KEY: misc_feature
        ( B ) LOCATION: 1..24
        ( D ) OTHER INFORMATION: /note= "probe MTB016 complementary to pre-23S rRNA open region target sequence -35 to -12 residues upstream of the mature 23S rRNA 5'terminus"

( x i ) SEQUENCE DESCRIPTION: SEQ ID NO:79:

CACGCCACCG CTAGCCGGCA GCGT                                                                 24

( 2 ) INFORMATION FOR SEQ ID NO:80:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium tuberculosis ( i x ) FEATURE:
        ( A ) NAME/KEY: misc_feature
        ( B ) LOCATION: 1..26
        ( D ) OTHER INFORMATION: /note= "probe MTB017 complementary
            to pre-23S rRNA open region target
            sequence -51 to -26 residues upstream
            of the mature 23S rRNA 5'terminus"

( x i ) SEQUENCE DESCRIPTION: SEQ ID NO:80:

GGCAGCGTAT CCATTGATGC TCGCAA                                                               26

( 2 ) INFORMATION FOR SEQ ID NO:81:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium tuberculosis ( i x ) FEATURE:
        ( A ) NAME/KEY: misc_feature
        ( B ) LOCATION: 1..22
        ( D ) OTHER INFORMATION: /note= "probe MTB018 complementary
            to pre-16S rRNA open region target
            sequence -58 to -36 residues upstream
            of the mature 16S rRNA 5'terminus"

( x i ) SEQUENCE DESCRIPTION: SEQ ID NO:81:

CAAACGGCCA CGCCCCCCAC AA                                                                   22

( 2 ) INFORMATION FOR SEQ ID NO:82:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium tuberculosis ( i x ) FEATURE:
        ( A ) NAME/KEY: misc_feature
        ( B ) LOCATION: 1..28
        ( D ) OTHER INFORMATION: /note= "probe MTB030

( x i ) SEQUENCE DESCRIPTION: SEQ ID NO:82:

ACCCAAACAC TCCCTTTGGA AAAGGG                                                               26

( 2 ) INFORMATION FOR SEQ ID NO:83:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Mycobacterium tuberculosis ( i x ) FEATURE:
( A ) NAME/KEY: misc_feature
( B ) LOCATION: 1..28
( D ) OTHER INFORMATION: /note= "probe MTB024 complementary
to pre-16S rRNA open region target
sequence +97 to +123 residues
downstream of the mature 16S rRNA 3'
terminus"

( x i ) SEQUENCE DESCRIPTION: SEQ ID NO:83:

CCTCAGGACC CAACAGTGTG TTGGTGGC 28

( 2 ) INFORMATION FOR SEQ ID NO:84:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Mycobacterium tuberculosis ( i x ) FEATURE:
( A ) NAME/KEY: misc_feature
( B ) LOCATION: 1..23
( D ) OTHER INFORMATION: /note= "probe MTB027 complementary
to pre-16S rRNA open region target
sequence +1 to +23 residues downstream
of the mature 16S rRNA 3'terminus"

( x i ) SEQUENCE DESCRIPTION: SEQ ID NO:84:

GGGGCGTTTT GCTGGTGCTC CTT 23

( 2 ) INFORMATION FOR SEQ ID NO:85:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Mycobacterium tuberculosis ( i x ) FEATURE:
( A ) NAME/KEY: misc_feature
( B ) LOCATION: 1..25
( D ) OTHER INFORMATION: /note= "probe MTB035 complementary
to pre-16S rRNA open region target
sequence +75 to +99 residues downstream
of the mature 16S rRNA 3'terminus"

( x i ) SEQUENCE DESCRIPTION: SEQ ID NO:85:

TGGCCAACTT TGTTGTCATG CACCC 25

( 2 ) INFORMATION FOR SEQ ID NO:86:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( v i ) ORIGINAL SOURCE:
      ( A ) ORGANISM: Mycobacterium tuberculosis ( i x ) FEATURE:
      ( A ) NAME/KEY: misc_feature
      ( B ) LOCATION: 1..20
      ( D ) OTHER INFORMATION: /note= "probe UP041 complementary
            to mature 16S rRNA open region target
            sequence"

( x i ) SEQUENCE DESCRIPTION: SEQ ID NO:86:

CTGCTGCCTC CCGTAGGAGT                                                    20

( 2 ) INFORMATION FOR SEQ ID NO:87:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: rRNA ( v i ) ORIGINAL SOURCE:
            ( A ) ORGANISM: Mycobacterium tuberculosis ( i x ) FEATURE:
            ( A ) NAME/KEY: precursor_RNA
            ( B ) LOCATION: 1..25
            ( D ) OTHER INFORMATION: /note= "pre-16S rRNA open region target
                  sequence complementary to probe MTB035"

( x i ) SEQUENCE DESCRIPTION: SEQ ID NO:87:

GGGUGCAUGA CAAGAAAGUU GGCCA                                              25

( 2 ) INFORMATION FOR SEQ ID NO:88:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( i i ) MOLECULE TYPE: rRNA ( v i ) ORIGINAL SOURCE:
            ( A ) ORGANISM: Mycobacterium tuberculosis ( i x ) FEATURE:
            ( A ) NAME/KEY: precursor_RNA
            ( B ) LOCATION: 1..30
            ( D ) OTHER INFORMATION: /note= "pre-16S rRNA open region target
                  sequence complementary to probe MTB024"

( x i ) SEQUENCE DESCRIPTION: SEQ ID NO:88:

GGCCACCAAC ACACUGUUGG GUCCUGAGGC                                         30

( 2 ) INFORMATION FOR SEQ ID NO:89:

( i ) SEQUENCE CHARACTERISTICS:
            ( A ) LENGTH: 39 base pairs
            ( B ) TYPE: nucleic acid
            ( C ) STRANDEDNESS: single
            ( D ) TOPOLOGY: linear ( i i ) MOLECULE TYPE: rRNA -continued (  v i  ) ORIGINAL SOURCE:
            ( A ) ORGANISM: Mycobacterium tuberculosis (  i x  ) FEATURE:
            ( A ) NAME/KEY: precursor_RNA
            ( B ) LOCATION: 1..20
            ( D ) OTHER INFORMATION: /note= "pre-16S rRNA open region target
                sequence complementary to probe MTB015"

(  x i  ) SEQUENCE DESCRIPTION: SEQ ID NO:89:

UUCUUUGUGC AAUAUUUUUU UUCUUUGGUU UUUGUUGUG                                   3 9

RAPID AND SENSITIVE DETECTION OF ANTIBIOTIC-RESISTANT MYCOBACTERIA USING OLIGONUCLEOTIDE PROBE SPECIFIC FOR RIBOSOMAL RNA PRECURSORS

This is a division of application Ser. No. 08/485,602, filed Jun. 7, 1995 which is a continuation-in-part of application Ser. No. 08/261,068, filed Jun. 16, 1994, abandoned.

BACKGROUND OF THE INVENTION

TECHNICAL FIELD OF THE INVENTION

This invention relates to methods and oligonucleotide probes for use in the detection and identification of mycobacteria. The invention is particularly useful for detecting antibiotic resistant mycobacterial isolates. The oligonucleotide probes consist essentially of a segment of nucleic acid capable of selectively hybridizing under hybridizing conditions to the mycobacterial ribosomal RNA. Methods for detection, as well as diagnostic kits for the assay of these bacteria, are also disclosed.

Rapid identification of microbial pathogens has long been an important goal of diagnostic technology. A new challenge is posed by the spread of antibiotic resistance. In addition to identifying the pathogenic species, the clinician must now affirm the potential efficacy of standard antimicrobial treatments early in the treatment of each case. Delays and erroneous results associated with conventional antibiotic susceptibility tests frequently lead to the administration of ineffective treatments, which in turn leads to complications, added costs, and poor outcomes.

Antibiotic-resistant Mycobacterium strains present one of the most difficult diagnostic challenges. The genus Mycobacteria is composed of Gram-positive, acid-fast bacteria. Taxonomically, the Mycobacterium genus is divided into descriptive groups based on growth rate and pigmentation. Among these groups are the photochromogenic (pigmented) slow growers (Group I), the scotochromatic slow growers (Group II), the nonchromogenic slow growers (Group III), and the rapid growers (defined as maturing in less than one week) (Group IV) [Sommers and Good (1985) In E. H. Lennette et al. (Eds.), *Manual of clinical microbiology*, 4th ed., American Society for Microbiology, Washington D.C., pp. 216–248; Wayne and Kubica (1986) In PHA Sneath et al. (Eds.), *Bergey's manual of systematic bacteriology*, vol. 2, The Williams & Wilkins Co., Baltimore, pp. 1435–1457; both of which are incorporated herein by reference.

Both rifampin and kanamycin are important antituberculosis drugs. Resistance to these drugs is becoming increasingly prevalent, and rapid detection of resistant strains is becoming increasingly important for diagnosis and treatment of the disease.

Prior art methods used for testing the sensitivity of mycobacterial isolates to common antibiotics have serious shortcomings. The most common method involves isolating the pathogen from patient samples and applying culture-based tests for antibiotic-resistant growth using the proportion method or minimum inhibitory concentration (MIC). See, e.g., Good and Mastro (1984) *Clinics in Chest Medicine* 10: 315–322); Heifets (1988) *Ann Rev. Respir. Dis.* 137: 1217–1222. This process can take several weeks for slow-growing mycobacteria. This is much too long for use in planning therapy for a mycobacterial infection.

The need to wait for colony formation can be circumvented by using more rapid tests for metabolic activity in broth cultures challenged with antibiotics. The most common metabolic method is the BACTEC radiometric system (Becton Dickinson), which detects mycobacterial conversion of $^{14}C$-palmitic acid to $^{14}CO_2$. See, e.g., Siddiqi et al. (1985) *J. Clin. Microbiol.* 22: 919–923; Snider et al. (1981) *Ann Rev. Respir. Dis.* 123: 402–408. This method can be conducted on primary cultures of decontaminated sputum samples after incubation for several days to amplify cell numbers. However, this method requires equipment and licenses for working with radioisotopes. Furthermore, the clinically important step of identifying the particular species involved requires additional culture or DNA probe analysis.

Theoretically, one could simultaneously identify a mycobacterial species and determine whether it is sensitive to common antibiotics through use of more than one probe. One oligonucleotide probe would detect species-specific DNA or RNA sequences, while another probe detects common antibiotic resistance genes. However, this method is useful only for known antibiotic resistance genes. Many different mechanisms can result in antibiotic resistance; many of these are not well understood. For example, resistance of *M. tuberculosis* to isoniazid can arise through mutations that reduce the expression of the catalase-peroxidase (katG) gene, or through separate mutations that enhance the expression of the inhA gene [Zhang et al. (1992) *Nature* 358: 591–593]. Similarly, resistance to rifampin can arise through any of a large number of missense mutations scattered over 1000 bases of the rpoB gene [Telenti et al. (1993) *The Lancet* 341: 647–650]. Because of such diversity, genetic probing techniques are frequently less useful than phenotypic tests for antibiotic effectiveness, such as the culture or BACTEC methods, which can detect resistance regardless of its genetic basis.

Each of the above methods of detecting antibiotic-resistant mycobacterial isolates lacks one or more of the following criteria necessary for a routine diagnostic assay: 1) cost (inexpensive); 2) batch capability; 3) speed (hours, not days or weeks); 4) sensitivity; 5) specificity; 6) ability to both identify the mycobacterium species and to determine whether the mycobacterium is resistant to antibiotics in one test; and 7) ability to detect drug-resistant mycobacteria regardless of the genetic basis for resistance. Consequently, there is a need in the art for alternative detection methodologies that are both fast and sensitive to a wide range of mycobacteria.

INFORMATION DISCLOSURE

Previously described methods for identifying the species to which cells of a mycobacterial sample belong have serious shortcomings. Many species are not discernable by classical techniques, such as hybridization using oligonucleotide probes specific for the mature 16S rRNA. For example, a commonly used DNA probe test for identification of Mycobacterium species, the Gen-Probe Rapid Diagnostic System, can differentiate species in the clinically important *Mycobacterium tuberculosis* complex from species in the *Mycobacterium avium* complex, but cannot differentiate one species within the *M. tuberculosis* complex from another (e.g. *M. tuberculosis* from *M. bovis*). This is because the mature 16S rRNA sequences targeted by the test are essentially identical within the *M. tuberculosis* complex [Kempsell et al. (1992) *J. Gen. Microbiol.* 138: 1717–1727]. Thus, even when this sophisticated DNA probe system is used, each isolate must be further analyzed by slower, more conventional biochemical methods to make a final species identification.

Similarly, previously described methods for determining antibiotic sensitivity are also problematic when applied to the mycobacteria. One such method for detecting antibiotic sensitivity involves determining the steady-state levels of precursor ribosomal RNA (pre-rRNA) in cells exposed to the antibiotic [see, e.g., Kohne, European Patent Application 0 531 798, which is incorporated herein by reference]. This method is advantageous over those described above in that the assay does not depend upon extensive growth of the cells. However, for reasons discussed below, this assay has not previously been usable for mycobacteria.

The mycobacterial ribosomal RNA operon is arranged similarly to those of other eubacteria. Typically, the mycobacterial rrn operon is arranged as follows (from 5' to 3'): Leader region, 16S rRNA gene, intergene spacer-1, 23S rRNA gene, intergene spacer-2, 5S rRNA gene. See, e.g., Ji et al. (1994) *Microbiology* 140: 123–132. Slow growing mycobacteria tend to have a single rrn operon, while faster growing species tend to have multiple rrn operons [Bercovier et al. (1986) *Biochem. Biophys. Res. Commun.* 136: 1136–1141].

Steady state levels of precursor rRNA drop in response to antibiotics that inhibit RNA synthesis. This effect is caused by the particular point at which the antibiotic inhibits the mechanism by which rRNA is processed in the cell. During post-transcriptional processing of bacterial ribosomal RNA, RNase III cleaves primary transcripts that are derived from bacterial rrn operons, but leaves tails on the resulting pre-rRNA molecules. The tails are removed from this pre-rRNA during the secondary steps in rRNA processing to yield the mature rRNA [see, e.g., King et al. (1986) *Microbiol. Rev.* 50: 428–451]. Because the first processing step occurs much faster than the second, the steady-state levels of pre-rRNA molecules are generally much higher than the levels of the primary transcripts. Thus, pre-rRNA is often detectable experimentally, whereas the primary transcripts are not.

Previous studies, mostly using *E. coli* as a model system, have demonstrated that pre-rRNA copy number rapidly decreases in sensitive cells that are treated with certain antibiotics that inhibit RNA synthesis [Srivastava et al. (1990) in *The Ribosome: Structure, Function, and Evolution*, W. E. Hill et al. (Eds.), American Society for Microbiology, Washington D.C., pp. 426–434; King et al. (1983) *J. Biol. Chem.* 258: 12034–12042]. Presumably, de novo pre-rRNA synthesis is inhibited while maturation proceeds.

Mycobacterial rRNA undergoes processing similar to that of other bacteria. However, prior to the present invention, pre-rRNA had never been detected in mycobacteria, despite many attempts. Researchers have advanced several hypotheses to explain this failure. One hypothesis is that the waxy cell wall of mycobacteria is unusually difficult to rupture. To detect pre-rRNA, one must first free the pre-rRNA from the cells. Methods sufficiently harsh to lyse the waxy mycobacterial cell wall might cause degradation of the cellular pre-rRNA.

Another hypothesis advanced to explain why pre-rRNA had never been detected in mycobacteria is that mycobacteria have a very low copy number of precursor rRNA. Ji et al., after failing to detect mycobacterial pre-rRNA, hypothesized that mycobacterial pre-rRNA is processed rapidly after transcription. Thus, the ratio of pre-rRNA to mature rRNA would be inversely proportional to the doubling time of a bacterium [Ji et al. (1994) *J. Infect. Diseases* 169: 305–312]. A third hypothesis is that the extensive secondary and tertiary structure of mycobacterial rRNA blocks hybridization of oligonucleotide probes.

To the clinician, it matters not which if any of these hypotheses is correct. What matters to the clinician is that, prior to the instant invention, one could not detect mycobacterial pre-rRNA. Thus, the methods described above for determining antibiotic sensitivity were not available. Given the above-discussed shortcomings of the other available methods, this has resulted in much difficulty in planning therapies against mycobacterial infection. Our invention provides a method for detecting mycobacterial pre-rRNA, and thus makes possible quick, sensitive methods for testing antibiotic sensitivity.

It is a further objective of this invention to provide rapid lysis methods for mycobacterium that release intact pre-rRNA molecules. Previously known methods for lysing mycobacterium involve processes requiring several days or involve the use and accompanying expense of a sonicator or other mechanical cell disrupter. Furthermore, as discussed above, no previously described method resulted in detectable levels of pre-rRNA. The claimed method has the further advantage of permitting one to detect precursor rRNA because the prior art methods are generally too slow and permit the precursor RNA to be degraded. One aspect of the instant invention is an enzymatic lysis method that takes less than two hours and can be routinely achieved in about 1 hour when optimized.

SUMMARY OF THE INVENTION

The present invention is directed to methods for lysing mycobacterium that free but do not degrade pre-rRNA. The methods involve treating the cells by enzymatic degradation using both lysozyme and a protease until their cell walls are made porous to expose their cell membranes and render the cells susceptible to lysis in the succeeding steps. The treated cells are contacted with a combination of a magnesium chelator, a nonionic detergent and an anionic detergent, and the cells are heated to between about between 75°–99° C. until the cells are lysed.

The invention also includes methods for detecting pre-ribosomal RNA (pre-rRNA) in cells of a mycobacterial sample. The methods comprise treating the cells by enzymatic or mechanical means to expose the cell membrane to lysis reagents, contacting the cells with a lysis reagent under conditions that release but do not degrade the pre-rRNA, and detecting the pre-rRNA using at least one oligonucleotide probe.

Also claimed are methods for determining whether cells of a mycobacterial sample are sensitive to an antimicrobial agent. The mycobacterial cells are incubated in the presence of the antimicrobial agent, after which the cells are treated by enzymatic or mechanical means to expose the cell membranes to lysis reagents. The cells are then contacted with a lysis reagent under conditions that release but do not degrade the mycobacterial pre-rRNA. The mycobacterial pre-rRNA is detected using an oligonucleotide probe. Sensitivity to the antimicrobial agent is indicated by an increase or a decrease in pre-rRNA levels for mycobacterial cells exposed to the antimicrobial agent compared to mycobacterial cells not exposed to the antimicrobial agent.

Oligonucleotide probes are also claimed. The claimed probes are between about 10 to 100 nucleotides in length and are capable of selectively hybridizing, under hybridizing conditions, to a region of a mycobacterial pre-rRNA molecule that is not present in a mature mycobacterial rRNA molecule.

The present invention also includes a device for detecting pre-rRNA in a mycobacterial sample. The device consists of an oligonucleotide probe, as described above, that is immobilized on a solid support. Also claimed is a kit for detecting pre-rRNA in a mycobacterial sample. The kit contains a device as described above and a second oligonucleotide probe that is between about 10 to 100 nucleotides in length and is capable of selectively hybridizing, under hybridizing conditions, to a region of a mycobacterial rRNA molecule to which the first oligonucleotide probe does not hybridize under hybridizing conditions.

The present invention is also useful for drug discovery. A method for determining the antimycobacterial efficacy of a compound is claimed. Mycobacterial cells are incubated in the presence of the compound. The cells are then treated by enzymatic or mechanical means to expose the cell membrane to lysis reagents, and contacted with a lysis reagent under conditions that release but do not degrade pre-rRNA from the cells. The amount of mycobacterial pre-rRNA is detected using an oligonucleotide probe. Sensitivity to the compound is indicated by an increase or a decrease in pre-rRNA levels for mycobacterial cells exposed to the compound compared to mycobacterial cells not exposed to the compound. The sensitivity of the method can be improved by depleting the mycobacterial cells of pre-RNA prior to contact with the test compound. Typical means for depletion are be limiting a nutrient or by exposing the mycobacterial cells to a second antibiotic compound which is other than the test compound and then removing the second compound prior to contact with the test compound where the cells would otherwise recover from the exposure to the second antibiotic and again produce pre-RNA.

BRIEF DESCRIPTION OF THE FIGURES

FIG. 3. Diagram showing the elements of an rRNA hybridization "sandwich" assay.

FIG. 4. Results of a chemiluminescent sandwich assay for M. tuberculosis pre-16S rRNA. The experiment was performed as described in Example 4.

DESCRIPTION OF THE PREFERRED EMBODIMENT

Figure 1:
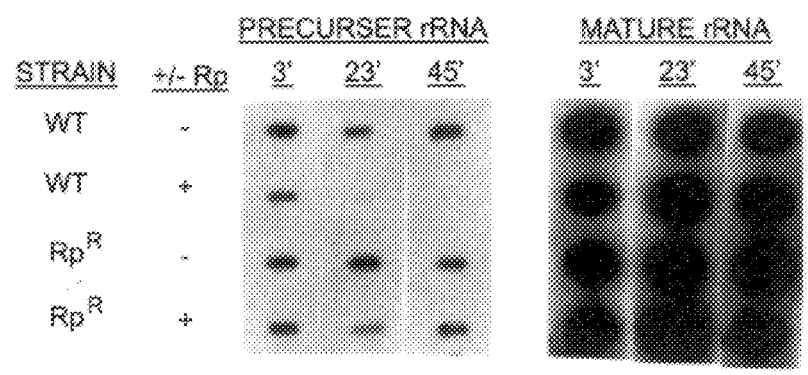
FIG. 1. Detection of precursor and mature E. coli 16S ribosomal RNA in a slot blot hybridization experiment. Cultures of rifampin-sensitive (WT) and rifampin-resistant ($Rp^R$ E. coli cells were treated with rifampin dissolved in dimethylsulfoxide (+Rp) or dimethylsulfoxide alone (–Rp), as described in Example 1. Time (minutes) after treatment is shown.

This invention relates to methods for characterizing Mycobacteria, both in terms of identifying particular species and determining whether a particular isolate is resistant to an antibiotic. The methods combine the comprehensive sensitivity of phenotypic tests for antibiotic susceptibility with the speed and species specificity of oligonucleotide probe methods. Also included in the invention are oligonucleotide probes suitable for use in the claimed methods, and methods for freeing precursor ribosomal RNA from mycobacterial cells.

Mycobacterial Cell Lysis

The invention also provides very rapid methods for thoroughly disrupting mycobacterial cells, inactivate nucleases, and release the pre-rRNA. Importantly, the claimed lysis methods release the pre-rRNA without also degrading the pre-rRNA. The claimed methods avoid the pre-rRNA degradation that characterize previously described mycobacterial lysis methods. Because of this degradation, pre-rRNA could not be detected using these earlier methods. One can utilize the hybridization methods described below to determine whether the lysis experiment has released intact pre-rRNA.

The claimed lysis methods, which are outlined in Table 1 (along with a prior art method), involve three basic steps. In summary, the cells are first subjected to a brief pre-treatment (enzymatic or mechanical) to weaken the cell walls. Next, a brief lysis step is performed during which the samples are heated in the presence of detergents. Finally a chaotropic salt solution is added to the lysate to stabilize the released pre-rRNA. The total time from culture to lysate is under 45 minutes. The lysis methods of this invention are useful for cells of many mycobacterial species, including M. tuberculosis, M. leprae, M. habana, M. avium, M. bovis, M. lufu, M. paratuberculosis, M. inarinum, M. simiae, M. intracellulare, M. genavense, M. malmoense, M. scrofulaceum, M. kansasii, M. cheloni, M. fortuitum, and M. xenopi. The taxonomy of the Mycobacteria is not static. Type cultures are available from the American Type Culture Collection (ATCC), Rockville, Md. As other mycobacteria are identified or other subtypes are differentiated from the above list, the disclosed invention readily provides methods for preparing pre-rRNA and oligonucleotide probes of sufficient specificity for use in identifying these bacteria and determining their sensitivity to antimicrobial agents.

One can use mycobacterium either from a culture, or from a clinical sample that is not cultured under in vitro conditions. The modified Du Bos medium is preferred for culturing mycobacterium. A general reference disclosing conventional means to culture mycobacterium is Good and Mastro, supra., and Heifets, supra.

TABLE 1. METHODS FOR OBTAINING NUCLEIC ACID FROM MYCOBACTERIA

Table 1a. Ji et al. (1994)
1. Grow bacteria 2 weeks at 37° C. on Modified Du Bos medium.
2. Add glycine to 0.2M and culture for 2 more weeks (to modify cell walls).
3. Harvest cells by centrifugation.
4. Wash cells twice in 50 mM Tris/HCl, 10 mM EDTA, 0.3M sucrose, and resuspend in same buffer.

5. Add Lipase and lysozyme to 2 mg/ml, and incubate 2 h at 37° C.
6. Centrifuge cells and resuspend in 6M guanidinium chloride, 0.1% Tween 80, 10 mM EDTA, and 1 mM 2-mercaptoethanol, and store at −20° C. for 16 h.

Total time: 2 week pre-treatment+18 hour lysis procedure.

Table 1b. Rapid sonication method

1. Grow bacteria 2 weeks at 37° C. on Modified Du Bos medium.
2. Harvest cells by centrifugation.
3. Resuspend in 50 mM sodium acetate, 10 mM EDTA, and 1% 2-mercaptoethanol.
4. Sonicate the cells in the presence of 75–150 $\mu$M glass beads (Sigma Chemical Company) in an ultrasonic cleaner (Ney ULTRAsonik 300; Bloomfield, Conn.) for 30 minutes.
5. Centrifuge cells and resuspend in lysis buffer (100 mM Tris, 10 mM EDTA, 2% Sarcosyl, 0.5% SDS, 0.1% Proclin, pH 7.5).
6. Heat for 5 minutes at 85° C.
7. Add 1.5 volumes of hybridization buffer (105 mM Tris, 10.5 mM EDTA, 8.79% formamide, 5.26M guanidinium thiocyanate, 2.1% sarcosyl, pH 7.5).

Total time: Approximately 45 minutes.

Table 1c. Rapid enzymatic method.

1. Grow bacteria 2 weeks at 37° C. on Modified Du Bos medium.
2. Harvest cells by centrifugation.
3. Resuspend in 1× TE buffer (pH 7.5).
4. Add lysozyme to 10 mg/ml and proteinase K to 0.1 mg/ml, and incubate for 30 minutes at 37° C.
5. Centrifuge cells and resuspend in lysis buffer (100 mM Tris, 10 mM EDTA, 2% Sarcosyl, 0.5% SDS, 0.1% Proclin, pH 7.5).
6. Heat for 5 minutes at 85° C.
7. Add 1.5 volumes of hybridization buffer (105 mM Tris, 10.5 mM EDTA, 8.79% formamide, 5.26M guanidinium thiocyanate, 2.1% sarcosyl, pH 7.5).

Total time: Approximately 45 minutes.

The cells can be concentrated prior to lysis. The specific means are not critical and include low speed centrifugation and filtration means. The concentrated cells are then resuspended into a low salt buffer comprising a divalent chelator and having a pH of about 4.5 to 8.0. The buffer can optionally contain a reducing agent such as mercaptoethanol, dithiothreitol, or dithioerythritol, or a combination thereof. Suitable chelators include ethylenediamine tetraacetic acid (EDTA), ethylene glycol-bis(â-amino-ethyl ether)-tetraacetic acid (EGTA), and ethylene diimino dibutyric acid (EDBA).

Suitable buffers include, but are not limited to, brucine tetrahydrate, 4-(2-hydroxyethyl)-1-piperazinepropane sulfonic acid, tris(hydroxymethyl) aminomethane, N-tris(hydroxy-methyl) methylglycine, glycinamide, N,N-bis(2-hydroxyethyl) glycine, N-tris(hydroxymethyl)methyl-2-aminopropane sulfonic acid, N-glycyl-glycine, histidine, boric acid, pyrophosphoric acid, ethanolamine, glycine, trimethylamine, cyclopetanetetra-1,2,3,4-carboxylic acid, carbonic acid, 3-cyclohexylamino-1-propanesulfonic acid, EDTA, methylamine, dimethylamine, ethylamine, triethylamine, diethylamine, ascorbic acid, and phosphoric acid, sodium acetate, and Tris.

The cells are then treated to perturb or compromise the integrity of the cell wall. This exposes the cell membranes to the lysis reagent, which is added in a succeeding step. In one preferred embodiment, the mycobacterium cell wall is treated by enzymatic digestion. The resuspended cells are treated with a combination of lysozyme (5–20 mg/ml) and an endoprotease such as PRONASE or proteinase K (0.5 to 0.05 mg/ml) (Sigma Chemical Co., St. Louis Mo.) ."Lysozyme" refers to enzymes that attack bacterial cell walls by hydrolyzing the â(1–4) linkages between N-acetyl-D-muramic acid and 2-acetylamino-2-deoxy-D-glucose residues. Lysozyme also acts on chitin. "Protease" refers to enzymes that catalyze the breakdown of proteins. "PRONASE" is a nonspecific protease isolated from *Streptomyces griseus*.

The amounts of enzymes and the duration of enzyme treatment will depend upon the temperature and the amount of mycobacterium present. In general, for $5 \times 10^9$ mycobacterial cells/ml or less, about 10 mg/ml lysozyme and 0.1 mg/ml proteinase K is sufficient with a 20–40 minute incubation at 37° C. A lipase can be optionally added.

In another preferred embodiment, the treatment is by mechanical means. The mycobacterial cells are resuspended in buffer as above, glass beads are added, and the cells are sonicated. Typically, the sonication is performed on a Ney UltraSonik sonicator at "full" setting for 20–60 minutes (J. M. Neyn Co., Bloomfield Conn.).

The treatment is performed until the mycobacterial cell walls are rendered porous to expose cell membranes making the cells susceptible to lysis in the succeeding steps. One can test to determine whether treatment is complete simply by adding the lysis reagent to an aliquot of the treated cells, heating, and observing whether the cells are lysed. One can make this observation by determining whether cellular contents such as nucleic acids are released.

Following the enzymatic or mechanical treatment, the cell lysis is completed by adding to the cell suspension a lysis reagent that contains a detergent and incubating the suspension at high temperature. The lysis reagent typically has a pH between 6.5 and 10.5, with a pH of about 7.5 being preferred. Suitable buffers include those listed above for the resuspension buffers. Suitable detergents include anionic, cationic, or nonionic detergents, or combinations thereof. In a preferred embodiment, the buffer contains between 1%- and 5% (w/v) N-lauroylsarcosine and between 0% and 1% lauryl sulfate. The lysis buffer also preferably contains a chelating agent such as EDTA or EGTA. A reducing agent such as â-mercaptoethanol, dithiothreitol, or dithioerythritol, or a combination thereof, is also preferably included in the lysis buffer. PROCLIN (Supelco, Inc. Bellefonte, Pa.) can also be added to the lysis buffer as a preservative.

The cell suspension is incubated at between 75–99° C. until suitable lysis is observed. Following the above guidelines, one of skill using routine titration experiments can optimize the lysis conditions for any mycobacterium at any concentration. Typically, the suspension will be incubated for about five minutes or longer at 85° C.

The degree of cell lysis can be determined by the detection of released nucleic acid. The methods for such detection are not critical. The hybridization assays described herein are suitable for detecting release of nucleic acids.

Nucleic Acid Hybridization Methods

A significant advantage of the claimed invention is that it incorporates rapid and convenient sample-handling and detection methods. In one embodiment, hybridization assays are conducted directly on bacterial lysates, without the need to extract the nucleic acids. This eliminates several steps from the sample-handling process and speeds up the assay.

To perform such assays on crude cell lysates, a chaotropic agent is typically added to the cell lysates prepared as described above. The chaotropic agent stabilizes nucleic acids by inhibiting nuclease activity. Furthermore, the chaotropic agent allows sensitive and stringent hybridization of short oligonucleotide probes to RNA at room temperature [Van Ness and Chen (1991) *Nucl. Acids Res.* 19: 5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Alternatively, one can purify the pre-rRNA prior to probe hybridization. A variety of methods are known to one of skill in the art (e.g. phenol-chloroform extraction, IsoQuick extraction (MicroProbe Corp., Bothell, Wash.), and others). Pre-hybridization purification is particularly useful for standard filter hybridization assays (as described in Example 1). Furthermore, purification facilitates measures to increase the assay sensitivity by incorporating in vitro RNA amplification methods such as self-sustained sequence replication (3SR, NASBA) [Fahy et al. (1991) in *PCR Methods and Applications*, Cold Spring Harbor Laboratory Press, pp. 25–33] or reverse transcriptase PCR [Kawasaki (1990) in *PCR Protocols: A Guide to Methods and Applications*, M. A. Innis et al., eds., pp. 21–27].

Such assays using amplified pre-rRNA are another aspect of the claimed invention. Because of the increased sensitivity of assays that employ amplified pre-rRNA, culturing of the cells is not required. Clinicians can detect pre-rRNA in primary cultures or sputum samples without having to culture the cells for a significant amount of time to obtain detectable amounts of material. This is a significant advantage because it could take many days to obtain enough slow-growing Mycobacterium cells to carry out antibiotic susceptibility testing by the prior art methods.

One can obtain amplified pre-rRNA by using in vitro RNA amplification techniques such as NASBA (3SR) or RNA-PCR [Fahy et al., supra.; Kawasaki, supra.]. The exact procedure used is not crucial, provided that it does not amplify significant amounts of DNA, which would tend to obscure results. The use of amplified pre-rRNA in the claimed assays enables clinicians to obtain species detection and antibiotic susceptibility results within a day or two of obtaining a patient sample.

Once the pre-rRNA is released from the cells, it can be detected by any of a variety of methods. The method of pre-rRNA detection is not crucial to the invention. However, the most useful embodiments have at least some of characteristics of speed, convenience, sensitivity, and specificity. Direct DNA probe analysis is suitable, as is an in vitro RNA amplification method, such as 3SR, that employs labelled primers.

Hybridization Conditions

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/ml, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

In one preferred embodiment, nucleic acids from GuSCN-lysed bacteria can be immobilized directly onto nitrocellulose or Nytran, and hybridized with the appropriate probe. The GuSCN-lysate is diluted with buffer containing formaldehyde, slotted to nitrocellulose and heated at 80° C. to denature the nucleic acids. The hybridization solution comprises about 2 to 4M GuSCN, preferably 3M, about 0.01 to 0.1M Tris (pH range about 6.0 to 8.5), a detergent such as sodium dodecyl sulfate in concentrations of about 0.1 to 5% (w/v), and about 0.01 to 0.1M EDTA. Other additives may also be included such as carrier DNA or RNA, or protein such as bovine serum albumin or gelatin. Stringency of the hybridization solution can be adjusted by the addition of about 0 to 10- formamide, usually 5%. The hybridization is typically carried out for between 15 minutes and 16 hours, with about 1 hour being optimal. Hybridization and wash conditions are as described in Van Ness and Chen, supra.; Van Ness et al. (1991) *Nucl. Acids Res.* 19: 3345–3350; Cangelosi et al. (1993) *Molecular and Cellular Probes* 8: 73–80; and Dix et al. (1990) *J. Clin. Microbiol.* 28: 319–323.

In a particularly advantageous embodiment, the presence of a chaotropic agent in the hybridization solution permits hybridization under non-denaturing conditions, such as at room temperature. Because the strong secondary and tertiary structure that characterizes rRNA and pre-rRNA prevents many oligonucleotide probes from hybridizing, the rRNA must typically be denatured prior to hybridization. Experiments are thus somewhat of a balancing act, where one must maintain conditions under which the probe can hybridize but the rRNA does not lapse back into its usual secondary structure.

This balancing of conditions is not required when certain probes are used in a hybridization solution that contains a chaotropic agent such as guanidinium thiocyanate. After the initial heating step to lyse the cells, further heating to denature the nucleic acids just prior to the hybridization is not necessary. The elimination of the denaturation step greatly simplifies the assay and enhances reproducibility.

A sandwich assay is particularly adaptable to hybridization under non-denaturing conditions (FIG. 3). A primary component of a sandwich-type assay is a solid support. The solid support has adsorbed to it or covalently coupled to it immobilized nucleic acid probe that is unlabeled and complementary to one portion of the rRNA or pre-rRNA sequence. Preferred are those probes that hybridize to regions of the rRNA or pre-rRNA that have minimal secondary and tertiary interactions, such as those listed in Tables 2 to 4. The advantage of such probes is that the hybridization can be carried out without the additional step of heat denaturing the sample nucleic acid. For example, the hybridization can be carried out at room temperature.

The test sample containing mycobacteria is contacted with the solid support in a hybridization medium. Next, a second, soluble probe complementary to a different sequence of the rRNA or pre-rRNA of the mycobacteria is hybridized to the rRNA or pre-rRNA that has formed a hybridization duplex with the immobilized nucleic acid probe on the solid support. This second probe is typically labelled. The presence of pre-rRNA is then determined in accordance with the label being used. It should be noted that the second probe can be added simultaneously with the test sample to the hybridization assay. In addition, the second probe can hybridize to either a conserved or to a hypervariable region of the rRNA or pre-rRNA. Preferred are the probes derived from conserved regions of the ribosomal RNA or pre-rRNA that have minimal secondary and tertiary interactions. The advantage of such probes is that the hybridization can be carried out without the additional step of heat denaturing the nucleic acid. A general reference for various detection methods can be found in Hames, B. D. and Higgins, S. J., *Nucleic Acid Hybridization*, IRL Press, Oxford, 1985. References for sandwich assay with DNA probes are Dunn and Hassell (1977) Cell 12: 23–26; and Ranki et al., U.S. Pat. No. 4,486,539.

Hybridization techniques are generally described in *Nucleic Acid Hybridization: A Practical Approach*, Hames and Higgins, Eds., IRL Press, 1987; Gall and Pardue (1969) *Proc. Natl. Acad. Sci., USA,* 63: 378–383, and John, Burnsteil and Jones (1969) *Nature* 223: 582–587. As improvements are made in hybridization techniques, they can readily be applied. One such improvement is the subject of Ser. No. 130,754, our docket 11652-5, filed on Dec. 9, 1987, incorporated herein by reference, which relates to the use of ultrasonic energy to enhance the rate of hybridization. This is an optional step which does not influence the specificity of the probes described herein.

The amount of labeled probe which is present in the hybridization solution may vary widely, depending upon the nature of the label, the amount of the labeled probe which can reasonably bind to the cellular target nucleic acid, and the stringency of the hybridization medium and/or wash medium. Generally, substantial excesses of probe over the stoichiometric amount of the target nucleic acid will be employed to enhance the rate of binding of the probe to the target DNA.

Various degrees of stringency of hybridization can be employed. As the conditions for hybridization become more severe, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. Temperatures employed will normally be in the range of about 20° to 80° C., usually 30° to 75° C. For probes of 15–50 nucleotides in 50% formamide, the optimal temperature range can vary from 22° to 65° C. With routine experimentation, one can typically define conditions which permit satisfactory hybridization at room temperature.

The terms "stringent conditions" and "conditions of high stringency" refer to conditions under which a probe will hybridize substantially to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a complementary probe. Typically, stringent conditions will be those in which the salt concentration is at least about 0.2 molar at pH 7 and the temperature is at least about 60° C. for long sequences (e.g. greater than about 50 nucleotides) and at least about 42° C. for shorter sequences (e.g. 10 to 50 nucleotides). As other factors may significantly affect the stringency of hybridization, including, among others, base composition and size of the complementary strands, the presence of organic solvents and the extent of base mismatching, the combination of parameters is more important than the absolute measure of any one.

Assay test protocols for use in this invention are those of convention in the field of nucleic acid hybridization, and include both single phase, where the target and probe polynucleic acids are both in solution, and mixed phase hybridizations, where either the target or probe polynucleotides are fixed to an immobile support. The assay test protocols are varied and are not to be considered a limitation of this invention. A general review of single phase hybridization can be had from a reading of *Nucleic Acid Hybridization: A Practical Approach*, Hames and Higgins, eds., IRL Press, 1985; and *Hybridization of Nucleic Acids Immobilized on Solid Supports*, Meinkoth and Wah (1984) *Analytical Biochemistry*, pp. 238, 267–284. Mixed phase hybridizations are preferred.

Cultured colonies of the mycobacteria can be assayed using colony hybridization techniques, wherein the mycobacteria are plated and adsorbed onto a filter, after which the colonies are lysed and the pre-rRNA freed from the cells by the methods described herein. The filters are then exposed to the oligonucleotide probes (Grunstein and Hogness 1979 *Methods of Enzymology*, Ed. Ray Wu, Vol. 68, pp. 379–409; and *Proc. Natl. Acad. Sci. U.S.A.* 72: 3961–3965 (1975).

Regardless of the assay test protocol being used, the mycobacterial nucleic acids are to remain in contact with a hybridization solution at a moderate temperature for an extended period of time. In single phase assays, the double-stranded duplexes may be separated from single-stranded nucleic acid by S1 nuclease digestion followed by precipitation of duplex molecules, or by selective binding to hydroxyapatite. In mixed phase assays, the support-immobilized nucleic acids are introduced into a wash solution having analogous concentrations of sodium chloride, buffers, and detergent, as provided in the hybridization solution. The time period for which the support is maintained in the wash solution may vary from several minutes to three hours or more.

Either the hybridization or the wash medium can be stringent. Typically, for mixed phase assays, it is the wash solution that most often determines the stringency and facilitates dissociation of mismatched duplexes. After rinsing the support at room temperature with a dilute buffered sodium chloride solution, the support may now be assayed for the presence of duplexes in accordance with the nature of the label.

Where the label is radioactive, the presence of probe can be detected in a scintillation counter. More conveniently, in mixed phase assays, the substrate can be dried and exposed to X-ray film in any number of conventional autoradiographic protocols.

Where the label is fluorescent, the sample is detected by first irradiating it with light of a particular wavelength. The sample absorbs this light and then emits light of a different wavelength which is picked up by a detector (*Physical Biochemistry*, Freifelder, D., W. H. Freeman & Co., pp. 537–542, 1982).

Where the label is a hapten or antigen, the sample can be detected by using antibodies. In these systems, a signal is generated by attaching fluorescent or enzyme molecules to the antibodies; in some cases the antibody is labeled with a radioactive probe. (Tijssen, P. (1985) Practice and Theory of Enzyme Immunoassays, in *Laboratory Techniques in Biochemistry and Molecular Biology*, Burdon and van Knippenberg, Eds., Elsevier, pp. 9–20).

One method of detection is enzymatic detection in conjunction with biotin. Although fluorescence is an alternative label, enzymatic labels, in combination with avidin or streptavidin such as biotinylated peroxidase or alkaline phosphatase, are preferred. Enzyme-conjugated avidin or streptavidin can also be used to directly bind the enzyme to the probe [Haase et al. (1984) *Methods in Virology*, Vol. VII, pp. 189–226]. Preferred enzymes are peroxidase or alkaline phosphatase. An especially preferred method utilizes enzymes directly conjugated to probes. The preferred enzymes are alkaline phosphatase and peroxidase. Methods for conjugating enzymes to oligonucleotides are known. See, e.g., *Nucleic Acid Res.*, 14: 6115–6128 (1986) and *Nucl. Acid Res.*, 15: 5275–5287 (1987).

Oligonucleotide Probes

Oligonucleotide probes that are useful in the claimed methods comprise a further aspect of the invention. The claimed oligonucleotide probes are specific for ribosomal RNA precursor (pre-rRNA) molecules of mycobacterial species. Typically, the probes are between 10 and 100 nucleotides in length, and are capable of hybridizing substantially, under hybridizing conditions, to a region of a mycobacterial pre-rRNA molecule that is not present in a mature mycobacterial rRNA molecule. By "substantially", it is meant that under standard hybridization conditions of high stringency, percent hybridization can be shown to exceed 50% of the hybridization between perfectly complementary nucleic acid fragments. The probes selectively hybridize to pre-rRNA molecules, meaning that under standard hybridization conditions, the probes do not substantially hybridize to mature rRNA molecules.

Precursor rRNA sequences are known to have extensive secondary structure (intramolecular strand hybridization). This secondary structure is tenacious and chemical or heat denaturation will only temporarily disturb it. The secondary structure returns when the conditions are amended to allow probes to hybridize. While nucleotide sequence analysis has led researchers to hypothesize that single-stranded "open" regions exist in *E. coli* pre-rRNA molecules [Srivastava and Schlessinger (1990) In *The Ribosome Structure, Function and Evolution*, Hill et al., eds., American Society for Microbiol., Washington D.C., pp. 426–434]. These putative open regions are thought to have minimal secondary and tertiary interactions with other nucleotides.

The presence of open regions must be confirmed empirically. Researchers have postulated, again based on sequence analysis, that mycobacterial pre-rRNA also has single- and double-stranded regions [Kempsell et al. (1992) *J. Gen. Microbiol.* 138: 1717–1727; Ji et al. (1994) *Microbiology* 140: 123–132].

Particularly preferred oligonucleotide probes target open regions of the pre-rRNA. These regions are single-stranded under the hybridization conditions employed. Probes that target double-stranded regions result in decreased sensitivity and require a more complex assay. A double stranded target must first be denatured by heat or chemical treatment, after which the probes are added. Then, the solution is carefully returned to non-denaturing conditions, allowing the probe to hybridize to the target region. In contrast, probes that target single-stranded "open" regions allow one to carry out the entire assay in non-denaturing conditions, significantly improving convenience, economy, and sensitivity.

The probes of the invention, selectively hybridizing to open regions of mycobacterial pre-rRNA, function advantageously well in hybridization assays where the target RNA is not denatured just prior to hybridization. Examples of such oligonucleotides that are suitable for *M. tuberculosis* are listed in Table 2. One of skill can identify similar probes for additional mycobacterial species by performing a nucleotide sequence alignment in which the pre-rRNA nucleotide sequence of the new species is compared to the pre-rRNA sequence of a species for which suitable target regions are known. By comparing the two sequences, one can identify suitable target regions for the new species. Examples of such target regions are listed in Table 3. Some of the claimed probes (MTB017, MTB018, MTB024, MTB027, MTB030, and MTB034 (Table 2)) hybridize to mycobacterial pre-rRNA regions that, based on their nucleotide sequence, were previously thought to be double-stranded.

Certain of the claimed pre-rRNA-specific oligonucleotide probes are also useful for differentiating Mycobacteria species. These species-specific probes selectively hybridize to pre-rRNA molecules for one Mycobacterial species but not another. In this context, "selectively hybridizing" means that the oligonucleotides substantially hybridize, under standard hybridization conditions, to the complementary pre-rRNA region of the mycobacterial species for which the probe is specific but do not substantially hybridize to pre-rRNA of a different species. Standard hybridization conditions are of high stringency. Typically, these probes hybridize to hypervariable regions of the pre-rRNA, which are regions having a nucleotide sequence that is peculiar to a particular mycobacterial species or type.

Also claimed are certain species-specific oligonucleotide probes that selectively hybridize to the mature rRNA molecules of various mycobacterial species. Importantly, these claimed species-specific oligonucleotides that hybridize to mature rRNA molecules function well in hybridizations carried out under non-denaturing hybridization conditions, even though their target sequences are reported to be double-stranded under such conditions [Kempsell et al. (1992) *J. Gen. Microbiol.* 138: 1717–1727]. Table 4 lists target sequences having these properties that are suitable for various Mycobacteria species. Knowing the sequences of target regions that are effective for *M. tuberculosis*, one of skill can identify the homologous sequences from mature rRNA of other mycobacterial species by performing a nucleotide sequence alignment. See, e.g., Rogall et al. (1990) *Int. J. Syst. Bacteriol.* 40: 323–330.

The use of species-specific probes enables the clinician to identify a mycobacterial species and determine its antibiotic susceptibility even in the presence of other species. Thus, one can make the determination on a primary broth culture of a patient isolate. Colony isolation to obtain a pure culture is not required. If an in vitro RNA amplification method such as 3SR is employed, the experiment can be carried out directly on patient samples. Both of these methods represent a significant advance over the time-consuming methods of the prior art.

For example, it is clinically important to differentiate the *M. tuberculosis* complex from species in the *M. avium* complex. Making this differentiation by virtue of mature 16S rRNA sequence alone can be difficult, due to the greater than 98% similarity in sequence between the 16S rRNA molecules of the two complexes [Stahl and Urbance (1990) *J. Bacteriology* 172: 116–124; Rogall et al., supra.]. However, precursor rRNA sequences are only about 82% similar between the two complexes [Frothingham and Wilson, supra.]. Thus, DNA probes for pre-rRNA can more easily distinguish such closely-related groups of organisms than probes for mature rRNA. By choosing oligonucleotide probes or amplification primers that are sequence-specific, the clinician can easily differentiate pre-rRNA from mature rRNA, and also differentiate one species from another.

TABLE 2

Target and probe sequences for oligonucleotides specific for
Mycobacterium tuberculosis pre-rRNA molecules

| PROBE | DESCRIPTION | TARGET SEQUENCE (5'–3') | PROBE SEQUENCE (5'–3') |
|---|---|---|---|
| MTB015 | 5' pre-23S, −1 | UUCUUUGUGCAAUAUUUUUUUCUUUG UUUUUGUUGUG (SEQ. ID NO:89) | CACAACAAAAACCAAAGAATATTGCACAAAGAA (SEQ. ID NO:78) |
| MTB016 | 5' pre-23S, −35 | ACGCUGCCGGCUAGCGGUGGCGUG (SEQ ID NO:5) | CACGCCACCGCTAGCCGGCAGCGT (SEQ. ID NO:79) |
| MTB017 | 5' pre-23S, −51 | TTGCGAGCATCAATGGATACGCTGCC (SEQ ID NO:4) | GGCAGCGTATCCATTGATGCTCGCAA (SEQ ID NO:80) |
| MTB018 | 5' pre-16S, −58 | TTGTCGGGGGGCGTGGCCGTTTG (SEQ ID NO:7) | CAAACGGCCACGCCCCCCACAA (SEQ. ID NO:81) |
| MTB024 | 5' pre-16S, +96 | GGCCACCAACACACUGUUGGGUCCUGAGGC (SEQ. ID NO:88) | CCTCAGGACCCAACAGTGTGTTGGTGGC (SEQ. ID NO:83) |
| MTB027 | 5' pre-16S, +1 | AAGGAGCACCAGCAAAACGCCCC (SEQ. ID NO:10) | GGGGCGTTTTGCTGGTGCTCCTT (SEQ. ID NO:84) |
| MTB030 | 5' pre-16S, −1 | CCCUUUUCCAAAGGGAGUGUUUGGG (SEQ. ID NO:8) | ACCCAAACACTCCCTTTGGAAAAGGG (SEQ. ID NO:82) |
| MTB035 | 5' pre-16S, +75 | GGGUGCAUGACAAGAAAGUUGGCCA (SEQ. ID NO:87) | TGGCCAACTTTGTTGTCATGCACCC (SEQ. ID NO:85) |

Descriptions:
1) 5' or 3' refers to whether the target is on the 5' or 3' tail of the pre-rRNA;
2) pre-16S or pre-23S identifies the rRNA upon which the target sequence is located; and
3) Negative numbers refer to the number of nucleotides upstream of the mature rRNA 5' terminus that corresponds to the 3' end of the target sequence, and positive numbers refer to the number of nucleotides downstream of the mature rRNA 3' terminus that corresponds to the 5' end of the target sequence

TABLE 3

Target sequences for oligonucleotide probes specific for
pre-rRNA molecules of various Mycobacteria species

*M. tuberculosis*:

| | | |
|---|---|---|
| MTB027 | 5'AAGGAGCACCAGCAAAACGCCCCCC3' | (SEQ. ID NO:1) |
| MTB035 | 5'GGGUGCAUGACAACAAAGUUGGCCA3' | (SEQ. ID NO:2) |
| MTB024 | 5'GGCCACCACCACACUGUUGGGUCCUGAGGC3' | (SEQ. ID NO:3) |
| MTB017 | 5'UUGCGAGCAUCAAUGGAUACGCUGCC3' | (SEQ. ID NO:4) |
| MTB016 | 5'ACGCUGCCGGCUAGCGGUGGCGUG3' | (SEQ. ID NO:5) |
| MTB015 | 5'UUCUUUGUGCAAUAUUCUUUGGUUUUUGUUGUG3' | (SEQ. ID NO:6) |
| MTB018 | 5'UUGUCGGGGGGCGUGGCCGUUUG3' | (SEQ. ID NO:7) |
| MTB030 | 5'CCCUUUUCCAAAGGGAGUGUUUGGG3' | (SEQ. ID NO:8) |

*M. bovis*:

| | | |
|---|---|---|
| 1) | 5'AAGGAGCACCACGAAAACGCCCC3' | (SEQ. ID NO:9) |
| 2) | 5'GGGUGCAUGACAACAAAGUUGGCCA3' | (SEQ. ID NO:2) |
| 3) | 5'GGCCACCACCACACUGUUGGGUCCUGAGGC3' | (SEQ. ID NO:3) |
| 4) | 5'UUGCGAGCAUCAAUGGAUACGCUGCC3' | (SEQ. ID NO:4) |
| 5) | 5'GGCUAGCGGUGGCGUG3' | (SEQ. ID NO:11) |
| 6) | 5'UUCUUUGUGCAAUAUUCUUUGGUUUUUGUUGUG3' | (SEQ. ID NO:6) |

*M. avium*:

| | | |
|---|---|---|
| 1) | 5'AAGGAGCACCACGAAAAGCACCCC3' | (SEQ. ID NO:12) |
| 2) | 5'GGGUGCGCAACAGCAAAUGAUUGCCA3' | (SEQ. ID NO:13) |
| 3) | 5'GCCAGACACACUAUUGGGCCCUGAGAC3' | (SEQ. ID NO:14) |
| 4) | 5'UUGCGAGCAUCUAGAUGAGCGCAUGGU3' | (SEQ. ID NO:15) |
| 5) | 5'CGCAUGGUCUUCGUGGCCGGCGUUC3' | (SEQ. ID NO:16) |
| 6) | 5'AUCGAAAUGUGUAAUUUCUUUUUUAACUCUUGUG3' | (SEQ. ID NO:17) |
| 7) | 5'UGUGUGGGUAUGGCAA3' | (SEQ. ID NO:18) |
| 8) | 5'CUUGAUUUGAAAUUCACCUCGCUGCGCGAGGAGAU3' | (SEQ. ID NO:19) |

*M. lufu*:

| | | |
|---|---|---|
| 1) | 5'AAGGAGCACCACGAAAAGCUACCC3' | (SEQ. ID NO:20) |
| 2) | 5'GGGUGCAACAGCAAAUGAUUGCCA3' | (SEQ. ID NO:21) |
| 3) | 5'GCCAGACACACUAUUGGGCCCUGAGAC3' | (SEQ. ID NO:14) |
| 4) | 5'UUGCGAGCUACUAGAUGAACGCGUAGU3' | (SEQ. ID NO.22) |
| 5) | 5'CGCGUAGUCCUUGGGGCUGACGAGUUC3' | (SEQ. ID NO:23) |
| 6) | 5'AUCGAAAUGUGUUAUUUCUUUUUUAACUCUUGUG3' | (SEQ. ID NO:24) |
| 7) | 5'UGUGUGGGUAUGGUUGU3' | (SEQ. ID NO:25) |
| 8) | 5'CUGAUUUGAAUUCACCUCGUUCUGCGAGGAGUU3' | (SEQ. ID NO:26) |

TABLE 3-continued

Target sequences for oligonucleotide probes specific for
pre-rRNA molecules of various Mycobacteria species

*M. intracellulare*:

1) 5'AAGGAGCACCACGAAAAGCACUCC3' (SEQ. ID NO:27)
2) 5'GGGUGCACAACAGCAAAUGAUUGCCA3' (SEQ. ID NO:21)
3) 5'GCCAGACACACUAUUGGGCCCUGAGAC3' (SEQ. ID NO:14)
4) 5'UUGCGAGCAUCUAGAUGAGCGCAUAGU3' (SEQ. ID NO:28)
5) 5'CGCAUAGUCCUUAGUGAUGCGUC3' (SEQ. ID NO:29)
6) 5'GUCGAAAUGUGUAAUUUCUUCUUUGGUUUUUGUG3' (SEQ. ID NO:30)
7) 5'UGUGUGGGUAUGGCAA3' (SEQ. ID NO:18)
8) 5'CUGAUUUGAAAUUCACCUCGUUCAUCGAGGAGUU3' (SEQ. ID NO:31)

*M. leprae*:

1) 5'AAGGAGCACCACGAAAAACACUCUAA3' (SEQ. ID NO:32)
2) 5'GGGUGCGCAACAGCAAAUAUCCA3' (SEQ. ID NO:33)
3) 5'CCAGACACACUGUUGGGUCCUGAGGC3' (SEQ. ID NO:34)
4) 5'UUGCGAGCAUCUAAAUGGAUGCGUUGUC3' (SEQ. ID NO:35)
5) 5'GCGUUGUCAGUUAUGUAGUGGUGGCGU3' (SEQ. ID NO:36)
6) 5'AUUCAUUGAAAAUGUGUAAUUUUCUUCUUUGGUUUUGUG3' (SEQ. ID NO:37)
7) 5'UGUGUGUAGGUGUAGUUUAUUA3' (SEQ. ID NO:38)
8) 5'CUAGAAAUUGAAAAUUUCGUCUAGUUAUUGAUGGAGUU3' (SEQ. ID NO:39)

*M. simiae*:

1) 5'AAGGAGCACCACGAGAAACACUCC3' (SEQ. ID NO:45)
2) 5'GGGUGCACAACAACAGGCAAUCGCCA3' (SEQ. ID NO:46)
3) 5'GCCAGACACACUAUUGGGCCCUGAGAC3' (SEQ. ID NO:14)

*M. paratuberculosis*:

1) 5'UGUGUGGGUAUGGCAA3' (SEQ. ID NO:18)
2) 5'CUGAUUUGAAAUUCACCUCGCUGCGCGAGGAGAU3' (SEQ. ID NO:40)

*M. marinum*:

1) 5'UGUGAGGGAGUAGUCGUU3' (SEQ. ID NO:41)
2) 5'CUGAUUGCGAAUUCACCUCGUUAUCGAGGGGUU3' (SEQ. ID NO:42)

*M. habana*:

1) 5'UGUGUAGGUAUGGUCGU3' (SEQ. ID NO:43)
2) 5'CAGAUUAUCUCUGAUUCGAAUCCACCUCGUUGAUCGAGGAGAU3' (SEQ. ID NO:44)

TABLE 4

Target sequences for oligonucleotide probes specific for
mature rRNA molecules of various Mycobacteria species

*M. tuberculosis*:

MTB001 5'CCAGUGGCCUAACCCUCGGGAGGGAGCUG3' (SEQ. ID NO:47)
MTB002 5'CGAACGGAAAGGUCUCUUCGGAGAUAC3' (SEQ. ID NO:48)
MTB004 5'AGGUCCGGGUUCUCUCGGAUUGACGGUA3' (SEQ. ID NO:49)

*M. bovis*:

1) 5'CCAGUGGCCUAACCCUCGGGAGGGAGCUG3' (SEQ. ID NO:47)
2) 5'CGAACGGAAAGGUCUCUUCGGAGAUA3' (SEQ. ID NO:50)
3) 5'AGGUCCGGGUUCUCUCGGAUUGACGGU3' (SEQ. ID NO:51)

*M. avium*:

1) 5'CCAGUGGCCUAACCCUUUGGGAGGGAGCUG3' (SEQ. ID NO:52)
2) 5'CGAACGGAAAGGCCUCUUCGGAGGUAC3' (SEQ. ID NO:53)
3) 5'AGGUCCGGGUUUUCUCGGAUUGACGGUA3' (SEQ. ID NO:54)

*M. intracellulare*:

1) 5'CCAGUGGCCUAACCCUUGGGAGGGAGCUG3' (SEQ. ID NO:55)
2) 5'GAACGGAAAGNCCCUUCGGGUAC3' (SEQ. ID NO:56)
3) 5'AGGUCCGGGGGGGGGUUUUCUCGGAUUGACGGUA (SEQ. ID NO:57)

*M. leprae*:

1) 5'CCAGUGGCCUAACCCUCGGGAGGGAGCUG3' (SEQ. ID NO:47)
2) 5'CGAACGGAAAGGUCUCUAAAAAAAUCUUUUUUAGAGAUAC3' (SEQ. ID NO:58)
3) 5'AGGUCUGGGGGGGGGGGUUUUCUCGGAUUGACGGUA3' (SEQ. ID NO:59)

*M. simiae*:

1) 5'CCAGUGGCCUAACCUUUGGAGGGAGCUG3' (SEQ. ID NO:60)
2) 5'CGAACGGAAAGNCCCUUCGGGNUAC3' (SEQ. ID NO:61)
3) 5'AGCGCAAGUGACGGUA3' (SEQ. ID NO:62)

TABLE 4-continued

Target sequences for oligonucleotide probes specific for
mature rRNA molecules of various Mycobacteria species

*M. paratuberculosis*:

1) 5'CCAGUGGCCUAACCCUUUUGGCAGGGAGCUG3' (SEQ. ID NO:63)
2) 5'CGAACGGGGGGGAAAGGCCUCUUCGGAGGUAC3' (SEQ. ID NO:64)
3) 5'AGGUCCGGGUUUUCUCGGAUUGACGGUA3' (SEQ. ID NO:54)

*M. marinum*:

1) 5'CCAGUGGCCUAACCUUUGGGAGGGAGCUG3' (SEQ. ID NO:65)
2) 5'CGAACGGAAAGGUCUCUUCGGAGAUAC3' (SEQ. ID NO:48)
3) 5'AGGUUCGGGUUUUCUCGGAUUGACGGUA3' (SEQ. ID NO:66)

Probes can have sequences complementary to the target sequences listed in Tables 2 to 4, or their equivalent. One of skill will recognize that oligonucleotide probes complementary to specific subsequences of the target regions, but not to the entire target region, will also function in the claimed assays so long as such probes substantially hybridize to the target regions.

The probes can be used by themselves as a single unit for binding, or the probes may be comprised of additional sequences not having the capacity to bind to pre-rRNA. Probes comprising more than the short sequences, as offered in Tables 2 to 4, may have repeating units of the same sequence (e.g., concatemers of a sequence), a mixture of different sequences specific to one species of mycobacteria, and even a mixture of sequences that may be specific to one or more mycobacterial species.

If such probes are to contain concatemers of short sequences, said long probes will display the high hybridization specificity inherent in a "short" probe containing, for example, only 20 nucleotides. This concatemeric probe sequence could be contained within the cloning vector sequences and would have the structure given by the formula below.

Alternatively, the oligonucleotide probe can comprise a concatemer that has the formula [X-Y-Z]n, wherein:

a) X is a sequence of 0 to 100 nucleotides or nucleotide analogs that are not complementary to conserved or non-conserved regions of mycobacterial pre-rRNA;

b) Y is a sequence of 10 to 100 nucleotides or nucleotide analogs that are capable of hybridizing under hybridizing conditions to a region of the mycobacterial pre-rRNA that is not present in mature rRNA, such that Y may also comprise subsequences that are capable of hybridizing under hybridizing conditions to pre-rRNA of only one species of mycobacteria, of two species of mycobacteria, or to pre-rRNA of three or more species of mycobacteria;

c) Z is a sequence of nucleotides the same as or different from X, such that nucleotides or nucleotide analogs are not complementary to conserved or non-conserved regions of nucleic acid mycobacterial pre-rRNA; and d) n is 1–500, or more and, where n is greater than 1, Y can be the same or different sequences of nucleotides having said hybridization capability. The probe can be free or contained within a vector sequence (e.g., plasmids or single stranded DNA).

Suitable oligonucleotide probes include synthetic oligonucleotides, cloned DNA fragments, PCR products, and RNA molecules. The nature of the probe is not important, provided that it hybridizes specifically to pre-rRNA, and not to mature rRNA or other sequences.

The degree of complementarity (homology) required for detectable binding with the mature or precurcor rRNA of mycobacteria will vary in accordance with the stringency of the hybridization medium and/or wash medium. The degree of complementarity will optimally be 100 percent; however, it should be understood that minor variations in the rRNA may be compensated for by reducing the stringency of the hybridization and/or wash medium as described below. Thus, despite the lack of 100 percent complementarity under reduced conditions of stringency, functional probes having minor base differences from their rRNA targets are possible. Therefore, under hybridization conditions of reduced stringency, it may be possible to modify up to 60 of a given oligonucleotide probe while maintaining an acceptable degree of specificity. In addition, analogs of nucleosides may be substituted within the probe for naturally occurring nucleosides. This invention is intended to embrace these species when referring to polynucleic acid probes.

To obtain large quantities of DNA or RNA probes, one can either clone the desired sequence using traditional cloning methods, such as described in Sambrook et al. *Molecular Cloning: A Laboratory Manual*, Cold Spring Harbor, N.Y., 1989, or one can produce the probes by chemical synthesis using commercially available DNA synthesizers. An example of cloning would involve insertion of the cDNA for the ribosomal RNA into a replication vector, such as pBR322, M13, or into a vector containing the SP6 promotor (e.g., generation of single-stranded RNA using SP6 RNA polymerase), and transformation of a bacterial host. The oligonucleotide probes can be purified from the host cell by lysis and nucleic acid extraction, treatment with selected restriction enzymes, and further isolation by gel electrophoresis.

Oligonucleotide probes can be chemically synthesized using commercially available methods and equipment. For example, the solid phase phosphoramidite method can be used to produce short probes of between 15 and 50 bases. For this invention, it is preferred to chemically synthesize short DNA probes using the Model 380B DNA Synthesizer from Applied Biosystems, Foster City, Calif., using reagents supplied by the same company. Probes can be comprised of the natural nucleotide bases or known analogs of the natural nucleotide bases, including those modified to bind labeling moieties. Oligonucleotide probes that comprise thionucleotides, and thus are resistant to nuclease cleavage, are also suitable.

Probes can be labeled by any one of several methods typically used to detect the presence of hybrid polynucleotides. The most common method of detection is the use of autoradiography using probes labeled with 3H, 125I, 35S, 14C, or 32P, or the like. The choice of radioactive isotope depends on research preferences due to ease of synthesis, stability, and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The choice of label dictates the manner in which the label is bound to the probe. Radioactive probes are typically made using commercially available nucleotides containing the desired radioactive isotope. The radioactive nucleotides can be incorporated into probes, for example, by using DNA synthesizers, by nick translation with DNA polymerase I, by tailing radioactive DNA bases to the 3' end of probes with terminal deoxynucleotidyl transferase, by treating single-stranded M13 plasmids having specific inserts with the Klenow fragment of DNA polymerase in the presence of radioactive deoxynucleotides, dNTP, by transcribing from RNA templates using reverse transcriptase in the presence of radioactive deoxynucleotides, dNTP, or by transcribing RNA from vectors containing specific RNA viral promoters (e.g., SP6 promoter) using the corresponding RNA polymerase (e.g., SP6 RNA polymerase) in the presence of radioactive ribonucleotides rNTP.

The probes can be labeled using radioactive nucleotides in which the isotope resides as a part of the nucleotide molecule, or in which the radioactive component is attached to the nucleotide via a terminal hydroxyl group that has been esterified to a radioactive component such as inorganic acids, e.g., 32P phosphate or 14C organic acids, or esterified to provide a linking group to the label. Base analogs having nucleophilic linking groups, such as primary amino groups, can also be linked to a label.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, (Renz. M., and Kurz, K. (1984) A Colorimetric Method for DNA Hybridization. *Nucl. Acids Res.* 12: 3435–3444) and synthetic oligonucleotides have been coupled directly with alkaline phosphatase [Jablonski, E., et al. (1986) Preparation of Oligodeoxynucleotide-Alkaline Phosphatase Conjugates and Their Use as Hybridization Probes. *Nuc. Acids. Res.* 14: 6115–6128; and Li P., et al. (1987) Enzyme-linked Synthetic Oligonucleotide probes: Non-Radioactive Detection of Enterotoxigenic *Escherichia Coli* in Faeca Specimens. *Nuc. Acids Res.* 15: 5275–5287.]

Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol.

The oligonucleotide or polynucleotide acid probes of this invention can be included in a kit which can be used to rapidly determine the level of pre-rRNA in cells of a mycobacterial sample. The kit includes all components necessary to assay for the presence of the pre-rRNA. In the universal concept, the kit includes a stable preparation of labeled probes to pre-rRNA, hybridization solution in either dry or liquid form for the hybridization of target and probe polynucleotides, as well as a solution for washing and removing undesirable and nonduplexed polynucleotides, a substrate for detecting the labeled duplex, and optionally an instrument for the detection of the label.

A more specific embodiment of this invention embraces a kit that utilizes the concept of the sandwich assay. This kit would include a first component for the collection of samples from patients, vials for containment, and buffers for the dispersement and lysis of the sample. A second component would include media in either dry or liquid form for the hybridization of target and probe polynucleotides, as well as for the removal of undesirable and nonduplexed forms by washing. A third component includes a solid support upon which is fixed or to which is conjugated unlabeled nucleic acid probe(s) that is(are) complementary to a part of the precursor rRNA of the species of mycobacteria being tested. In the case of multiple target analysis more than one capture probe, each specific for its own ribosomal RNA or pre-rRNA, will be applied to different discrete regions of the dipstick. A fourth component would contain labeled probe that is complementary to a second and different region of the same rRNA or pre-rRNA strand to which the immobilized, unlabeled nucleic acid probe of the third component is hybridized.

The probe components described herein include combinations of probes in dry form, such as lyophilized nucleic acid or in precipitated form, such as alcohol precipitated nucleic acid or in buffered solutions. The label may be any of the labels described above. For example, the probe can be biotinylated using conventional means and the presence of a biotinylated probe can be detected by adding avidin conjugated to an enzyme, such as horseradish peroxidase, which can then be contacted with a substrate which, when reacted with peroxidase, can be monitored visually or by instrumentation using a calorimeter or spectrophotometer. This labeling method and other enzyme-type labels have the advantage of being economical, highly sensitive, and relatively safe compared to radioactive labeling methods. The various reagents for the detection of labeled probes and other miscellaneous materials for the kit, such as instructions, positive and negative controls, and containers for conducting, mixing, and reacting the various components, would complete the assay kit.

Testing Mycobacteria for Antibiotic Sensitivity

The claimed invention also includes methods for determining whether cells of a mycobacterial sample are sensitive or resistant to antimicrobial agents. Briefly, these methods include the steps of 1) culturing the mycobacterial cells in the presence of the antimicrobial agent, 2) freeing the pre-rRNA from the cells using the methods described above, and 3) determining the amount of pre-rRNA in the lysate using an oligonucleotide probe. Sensitivity to the antimicrobial agent is indicated by an increase or decrease in pre-rRNA levels for mycobacterial cells exposed to the antimicrobial agent compared to mycobacterial cells not exposed to the antimicrobial agent.

Whether pre-rRNA levels increase or decrease in response to the antimicrobial agent will depend upon the step in the mycobacterial rRNA processing pathway that is inhibited by the particular agent. For example, rifampin works by inhibiting pre-rRNA synthesis while allowing processing to proceed. Thus, rifampin causes a complete or near-complete depletion of pre-rRNA in susceptible cells.

Chloramphenicol, kanamycin, and other translation inhibitors have the opposite effect. Chloramphenicol inhibits pre-rRNA processing without affecting synthesis. Therefore, pre-rRNA copy number increases in chloramphenicol-sensitive cells in the presence of chloramphenicol. Provided that appropriate quantitative controls are conducted to measure pre-rRNA copy number relative to cell number, one can use the methods described herein to determine chloramphenicol resistance or sensitivity.

Briefly, this procedure is performed as follows. First, the sample is decontaminated by standard methods [Heifets (1988) Ann Rev. Respir. Dis. 137: 1217–1222]. Next, a broth culture tube containing antibiotics is inoculated with the sample, as are control tubes that contain no antibiotic. The tubes are incubated for a period sufficient to allow the drug to act on pre-rRNA copy number. This period can be as short as a day or less. A sample is removed and the cells are lysed using the methods described herein. The amount of pre-rRNA is then determined. If desired, one can extract the nucleic acids, after which an amplification step can be employed. The amplification step, as described above, permits an even shorter culture period.

Adjustment of antibiotic challenge conditions to allow assessment of pre-rRNA response to antibiotics which do not directly affect RNA synthesis Our invention as described above and in examples to follow is particularly useful for assessing susceptibility of slow-growing mycobacteria to rifampicin, a front-line anti-tuberculosis drug. As illustrated in Example 7, rifampicin reduced pre-rRNA to base-line levels within 3 hours of exposure, or within one fifth of a typical 16 hour generation time. This response may have been facilitated by direct inhibition of RNA polymerase activity by rifampicin, which would rapidly shut down de novo pre-rRNA synthesis while allowing processing or degradation of pre-rRNA to proceed. Response to the quinilone drug ciprofloxacin is somewhat slower. In both cases, however, responses are much faster than traditional indications of cell density or viability such as culture optical density or detection of mature rRNA.

In contrast, no measurable response to the antituberculosis drug isoniazid was observed under the conditions illustrated in Example 7 (data not shown). This suggests that inhibition of pre-rRNA synthesis does not exceed inhibition of pre-rRNA degradation or processing during exposure to this drug. Conditions which allow the application of our invention to this and similar drugs would be extremely useful.

To broaden the applicability towards different drugs, it is possible to deplete bacterial pre-rRNA prior to antibiotic exposure, and measure the ability of a test antibiotic to inhibit its replenishment. Pre-treatments to deplete pre-rRNA include limiting a nutrient that is essential to the organism's growth in culture. We have observed that bacterial pre-rRNA is depleted below detectable levels very soon after certain nutrients become limiting, typically before the cessation of visible cell growth and division. Pre-rRNA is rapidly replenished when limiting nutrients are restored and the bacteria prepare to resume growth (data not shown). Most or all bacteriostatic or bacteriocidal antibiotics, if applied to cultures prior to the restoration of limiting nutrients, would prevent replenishment of pre-rRNA. Susceptibility to these antibiotics is thus measured as the degree of inhibition of pre-rRNA replenishment after nutrient limitation and restoration.

In one embodiment of this principal, mycobacterial cells are suspended in a small volume of medium lacking one or more key nutrient. After approximately one day of incubation in this medium to allow depletion of pre-rRNA, the cells are exposed to the test antibiotic. A control culture not exposed to the antibiotic is run in parallel. Soon after antibiotic addition, the limiting nutrients are restored. Limiting nutrients that would supply nitrogen are representative of the nutrients which would deplete pre-RNA depletion. After another day of incubation, cells are lysed and assayed for pre-rRNA as described above and in examples below. Strains which are susceptible to the inhibitory effects of the antibiotic will display little or no replenishment of pre-rRNA relative to the control culture, whereas resistant strains will be indistinguishable from the control culture. This procedure lengthens the time course of the assay by a day or two, but enables clinicians to use our invention to test mycobacterial susceptiblity to virtually any antibiotic.

Alternative pre-treatments to deplete pre-rRNA prior to antibiotic challenge include the use of chemical agents that reversibly inhibit RNA synthesis in bacteria, such as N-thrichloromethylthio-4-cycloheximide (Luo and Lewis, Biochem. Pharmocol. 44: 2251–2258, 1992). The nature and composition of the pre-treatment is not important to this example, provided that it depletes pre-rRNA levels in mycobacterial cells, and that its effects can be reversed to allow measurable replenishment pre-rRNA upon its removal or cessation.

Drug Discovery

The present invention also provides a means for discovery of new anti-mycobacterial drugs. Prior to the instant invention, the slow growth rate of mycobacteria forced researchers to culture cells for several weeks in order to observe the effects of potential drugs. Because of this long incubation period, the potential drug compounds often degraded. Only unusually stable compounds could be found to have efficacy.

Using the claimed methods, drug developers can now identify compounds that are more effective, but less stable, than those previously identified. In less than one day, one can use the claimed assay for pre-rRNA to measure mycobacterial response to inhibitors of RNA and protein synthesis (approximately a third of all antibacterial drugs are in this category). Thus, the test compounds are much less likely to degrade before their effectiveness can be established. Once effective compounds are identified, one can enhance their stability, if required, by chemical modification.

Another advantage of the claimed methods in drug discovery is that the methods provide very precise measurements of the degree of antibiotic sensitivity. This quantitative aspect of the claimed invention is useful for determining effective dosages, among other things.

The following examples are offered by way of illustration and not by limitation.

EXAMPLES

Example 1

Determining sensitivity of a bacterium to an antimicrobial agent using pre-rRNA

Materials and Methods

Bacterial strains and culture conditions. $E.$ $coli$ type strain ATCC 11775 was grown in Luria broth or agar, supplemented with antibiotics as appropriate, and incubated aerobically at 37° C. We isolated three independent, spontaneously arising rifampin-resistant mutants (11775-R1, 11775-R4, and 11775-R7) by spreading approximately $1 \times 10^{10}$ cells onto agar plates containing 20 µg/ml rifampin, and incubating the plates for 1–2 days. Colonies that grew were single-colony purified by streaking twice on plates containing rifampin (Sigma Chemical Co., St. Louis, Mo.) and once on antibiotic-free medium.

Antibiotic challenge, harvest, and lysis. At the indicated time points, we pipetted 100 μl samples of *E. coli* cultures (typically $10^7$–$10^8$ cells) directly into microfuge tubes containing 150 μl of a lysis/hybridization solution (150 mM Tris, pH 7.5, 30 mM EDTA, 3% N-lauryl sarcosine, 0.3% sodium dodecyl sulfate, 8.3% formamide, and 5 M guanidinium thiocyanate). The cells were lysed by heating the tubes for 5 minutes in an 85° C. water bath. Lysates were returned to room temperature and either assayed immediately or stored at −20° C. for later analysis. Frozen lysates were thawed at room temperature, heated to 85° C., and allowed to return to room temperature before use.

DNA probe synthesis. We synthesized DNA probes using standard phosphoramidite chemistry on either an Applied Biosystems 380B or a Milligen 7500 automated DNA synthesizer, and purified as previously described [Van Ness et al. [(1991) *Nucl. Acids Res.* 19: 3345–3350; Van Ness and Chen (1991) *Nucl. Acids Res.* 19: 5143–5151].

Slot blot hybridization assays. Slot blot hybridization assays were carried out as described [Cangelosi et al. (1993) *Molecular and Cellular Probes* 8: 73–80; Dix et al. (1990) *J. Clin. Microbiol.* 28: 319–323]. Briefly, we extracted nucleic acids from 100 μl of *E. coli* lysates by phenol/chloroform extraction followed by ethanol precipitation. We then applied the nucleic acids to Nytran filters using a slot blot apparatus. We end-labeled DNA oligonucleotide probes with $^{32}$P using polynucleotide kinase and hybridized the probe to the filters for 6–12 hours, as described in Cangelosi et al., supra., and Dix et al., supra. After washing, we exposed the filters to Kodak X-Omat autoradiography film.

Chemiluminescent DNA probe sandwich assays. DNA probe sandwich assays consisted of capture probes tethered to activated nylon beads, biotinylated signal probes, washes, a streptavidin/alkaline phosphatase conjugate solution, a chemiluminescent substrate (Lumigen, Inc., Detroit, Mich.), and a Luminoskan luminometer (Labsystems, Finland). Assays were carried out in multi-well tissue culture plates using reagents and procedures described by Van Ness et al. (1991), supra. and Van Ness and Chen (1991), supra. 5'-Hexylamine-tailed oligonucleotides were biotinylated (signal probes) or activated and attached to nylon beads (capture probes) as described [Van Ness et al. (1991), supra.

Results

DNA probe design. Nucleotide sequences of *E. coli* 16S mature rRNA and pre-rRNA sequences have been published previously [Dams et al. (1988) *Nucl. Acids Res.* 16 (Suppl.): r87-r174; King et al. (1985) *Microbiol. Rev.* 50: 428–451; Klein et al. (1985) *J. Biol. Chem.* 260: 8114–8120]. The probes that we designed from these sequences and used in this study are summarized in Table 5. Probes EC012 and EC013 are specific for the 3' tail of the pre-rRNA. EC013 spans the 3' 16S rRNA terminus to include four nucleotides within the mature rRNA [Srivastava and Schlessinger (1990), supra, pp. 426–434]. However, hybridization under the conditions used here would require an intact precursor tail. Probe EC014 is specific for a portion of the 5' pre-rRNA tail which is predicted to lack the secondary (double-stranded) structure associated with most pre-rRNA sequences [Srivastava and Schlessinger, supra.]. This site was targeted to allow access of the probe to the RNA under the nondenaturing conditions of our chemiluminescent sandwich assay. Probes EC016, EC020, and UP042 are specific for regions within the mature 16S rRNA, and therefore hybridize to both precursor and mature molecules.

TABLE 5

DNA probes. Negative (−) position numbers are upstream of the 5' 16S rRNA terminus and positive (+) position numbers are downstream of the 3' 16S rRNA terminus. Other positions numbers are within the mature 16S rRNA, starting from the 5' end.

| PROBE | TARGET POSITION | SEQUENCE |
| --- | --- | --- |
| EC012 | +3 to +31 | 5'-GTGTGAGCACTACAAAGTACGCTTCTTTAA-3' (SEQ. ID NO:67) |
| EC013 | 1538 to +25 | 5'-GCACTACAAAGTACGCTTCTTTAAGGTAAG-3' (SEQ. ID NO:68) |
| EC014 | −102 to −73 | 5'-ACTTGGTATTCATTTTTCGTCTTGCGACG-3' (SEQ. ID NO:69) |
| EC016 | 456 to 475 | 5'-GCAAAGGTATTAACTTTACTCCCTTCCTCC-3' (SEQ. ID NO:70) |
| EC020 | 179 to 206 | 5'-GTCCCCCTCTTTGGTCTTGCGACGTTAT-3' (SEQ. ID NO:71) |
| UP042 | 1390 to 1409 | 5'-TGACGGGCGGTGTGTACAA-3' (SEQ. ID NO:72) |

Rate of pre-rRNA response to rifampin treatment. We used a slot blot hybridization assay to examine the rate of pre-rRNA decay in rifampin-treated cells. Cultures of rifampin-sensitive and rifampin-resistant *E. coli* strains 11775 and 11775-R1 in exponential growth were challenged by addition of rifampin to a final concentration of 20 μg/ml. Control cultures were treated with an equivalent volume of dimethyl sulfoxide, the solvent used to deliver rifampin to the test cultures. One hundred microliter were taken and lysed immediately (within 3 minutes) after challenge, and at various time points thereafter.

We extracted the nucleic acids from the lysates and applied them to Nytran filters. We probed the filters with radiolabeled probe EC013, which is specific for the 3' tail of the pre-16S rRNA. Replicate filters were hybridized with EC016, which detects both precursor and mature rRNA. Within 45 minutes of rifampin addition, precursor rRNA became undetectable by EC013 in rifampin-sensitive cells but not in rifampin-resistant cells (FIG. 1). Precursor rRNA remained detectable in untreated cultures of both strains. Probe EC016, which hybridizes to mature rRNA, could not distinguish resistant and sensitive cultures over the course of the experiment, as expected due to the bacteriostatic action of rifampin and the stability of mature rRNA.

We could detect rifampin sensitivity in less than the time required for control cultures to double in concentration. Control cultures not challenged with the drug doubled approximately every 60 minutes in this experiment, while pre-rRNA levels in sensitive strains decreased drastically in only 45 minutes. We observed similar rates of response using the probes EC012, which overlaps the recognition site for EC013, and EC014, which recognizes the 5' tail of the pre-16S rRNA.

Experiments with independently isolated rifampin-resistant mutants 11775-R4 and 11775-R7 yielded the same results as for 11775-Rl. We also observed similar results using cells in the early stationary phase of growth ($OD_{600}$ approximately 1.5), which had been centrifuged and resuspended in fresh medium containing rifampin (data not shown). This suggests that processing of pre-rRNA in older cultures resumes very rapidly after a nutritional shift-up. These results indicate that pre-rRNA is processed rapidly enough in a variety of cultures to make it a useful marker for measuring the response of bacterial cells to rifampin.

Magnitude of ore-rRNA response to rifampin treatment. In testing for antibiotic sensitivity, it is important that one be able to detect a small number of resistant mutants present in mixed populations with a large number of sensitive cells. To achieve this sensitivity using the claimed method, resistant cells in a population must have a pre-rRNA copy number sufficiently high to distinguish the resistant cells from the background signal from sensitive cells.

To test the sensitivity of the claimed method, we used a semiquantitative chemiluminescent sandwich assay that incorporated EC020 (hybridizes to mature rRNA) as a capture probe and precursor-specific EC014 as a signal probe. Positive results with such a "sandwich" require intact pre-rRNA. We challenged cultures that contained various mixtures of E. coli 11775 (wt) and 11775-R4 (rifampin resistant) with rifampin as described above. After a 90 minute incubation, we assayed for pre-rRNA.

Figure 2:
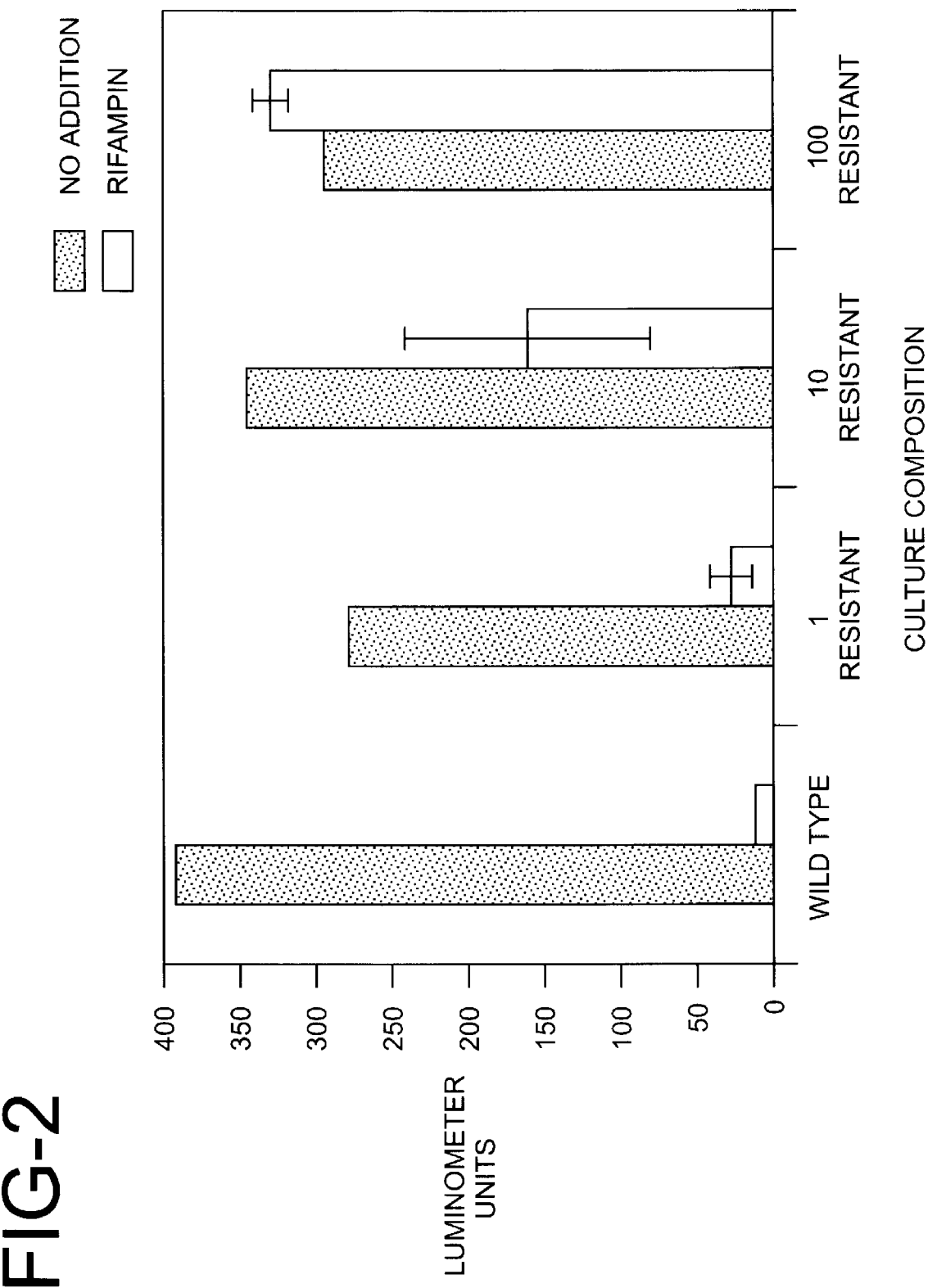
FIG. 2. Results of a chemiluminescent sandwich assay for precursor rRNA. Cultures of rifampin-resistant and rifampin-sensitive E. coli cells were mixed to obtain the indicated culture compositions. The cultures were immediately treated with rifampin dissolved in dimethylsulfoxide (light bars) or dimethylsulfoxide alone (dark bars), incubated for 90 minutes, and assayed for pre-rRNA as described in Example 4. Values for treated cultures are the means for three experiments.

In the absence of rifampin, cultures that we started with an initial inoculum of 100% sensitive cells were indistinguishable from cultures started from an initial inoculum of 1%, 10%, or 100% resistant cells (FIG. 2). When treated with rifampin, the culture containing 100% sensitive cells gave a very low signal, and cultures containing progressively higher percentages of resistant cells gave progressively stronger signals. Significantly, cultures containing as few as 1% resistant cells were reproducibly distinguishable from the 100% sensitive cultures. This result indicates that the magnitude of the response of pre-rRNA to rifampin challenge in susceptible E. coli cells is sufficient to make it a useful marker for sensitivity to the drug.

Example 2
Lysis of mycobacteria using an enzymatic treatment

The mycobacteria are cultured on modified DuBos medium to $1\times10^{11}$ cells. The cells are then harvested by low speed centrifugation and the pellet resuspended in 10 mM Tris-HCl, 1 mM EDTA, pH 7.5. The cells are then digested by lysozyme at a final concentration of 10 mg/ml and Protease K at 0.1 mg/ml. The mixture is then incubated for 30 minutes at 37° C.

The treated cells are then centrifuged and the pellet resuspended in 8 mls of lysis buffer consisting of 100 mM Tris, 10 mM EDTA, 2% Sarcosyl, 0.5% SDS, and 0.1% PROCLIN at pH 7.5. The lysis buffer is then heated to 85° C. for five minutes. The cell contents are now lysed and are ready for hybridization with mycobacterium-specific nucleic acid probes. The above lysis process can be conducted in about 45 minutes.

Example 3
Detection of M. tuberculosis pre-rRNA using a filter hybridization assay The purpose of this experiment was to determine if we were truly detecting a multi-copy pre-RNA molecule, as opposed to the chromosomal DNA molecules encoding it. This distinction is very important if pre-rRNA abundance is to be used as a measure of cellular response to antibiotics and other environmental conditions.

Experimental Outline. After immobilizing the M. tuberculosis RNA to a filter, we hybridized to it the probe MTB030, which selectively hybridizes to the 5' tail of the pre-16S rRNA, and to probe MTB530, which is the exact complement of MTB030 and is therefore specific for the DNA sequence that encodes the pre-rRNA.

Materials and Methods

We cultured M. tuberculosis cells for 10 days at 37° C. in DuBos medium, after which we lysed the cells using the enzymatic method described in Table lc. Total nucleic acid was extracted from the lysate as follows. The lysate was incubated at 37 for 5 minutes. An equal volume of m-pyrol (Boehringer Mannheim) was added, along with a 4× volume of extraction reagent (250% sucrose, 10 mM EDTA, 50 mM Tris-Cl). We heated the suspension for 10 minutes at 70° C. after adding an equal volume of phenol. We then vortexed the samples and centrifuged for 10 minutes at 12 krpm. We extracted the aqueous upper layer again with phenol, and precipitated the nucleic acid from the resulting aqueous layer by ethanol precipitation at −20° C. We dried the pelleted nucleic acid and resuspended in 1× Tris-EDTA buffer.

Nucleic acids from the equivalent of $5\times10^8$ cells were applied to a nytran filter using a slot blot apparatus (Schleicher and Schuell, Inc., Keene, NH), as described [Cangelosi et al. (1994) supra.; Dix et al. (1990) supra., both of which are incorporated herein by reference].

Oligonucleotide probes MTB030 and MTB530 were synthesized by standard phosphoramidite chemistry on a Milligen 7500 automated DNA synthesizer, and purified as previously described [Van Ness et al. (1991) supra. and Van Ness and Chen (1991) supra.]. Probes were end-labeled with $^{32}p$ using polynucleotide kinase and hybridized with the blotted nucleic acid, using standard techniques [Dix et al. (1990) supra.]. Hybridization was measured by autoradiography.

Results

Probe MTB030 hybridized strongly to the nucleic acids isolated from M. tuberculosis. However, probe MTB530 hybridized only weakly. This result indicates that the nucleic acids extracted from these cells contains a high copy number of pre-rRNA molecules (detected by MTB030), and a much lower copy number of chromosomal DNA molecules (detected by MTB530).

A drastic decrease in the ratio of pre-rRNA to DNA will be observed in sensitive cells treated with antibiotics that deplete pre-rRNA, such as rifampin. If the cells are resistant to the antibiotic, this drastic decrease will not be observed. Therefore, this procedure can be used to quickly assess bacterial response to rifampin and other compounds that inhibit RNA synthesis or processing, and to detect strains that are resistant to these compounds.

Example 4
Detection of M. tuberculosis pre-rRNA using a chemiluminescent sandwich assay Importantly for a rapid and convenient assay for pre-rRNA, denaturing of the pre-rRNA is not necessary. The assay incorporates oligonucleotide probes that selectively hybridize to single-stranded regions of the pre-rRNA.

Cells were cultured and lysed by the enzymatic method described in Table 1c. DNA probe MTB030 (5'-CCCAAACACTCCCTTTGGAAAAGGG-3')(SEQ. ID NO:72), which is specific for a single-stranded region of the 5' tail of the pre-16S rRNA, was synthesized and labeled with biotin as described [Van Ness et al. (1990) supra.]. Probe MTB002 (5'-GTATCTCCGAAGAGACCTT-TCCGTTCG-31)(SEQ. ID NO:74), which is specific for a single-stranded region present within the mature 16S rRNA, was synthesized with a 5' amine tail and tethered to nylon beads as described [Van Ness and Chen (1991) supra.; Van Ness et al. (1991) supra.]. We used these two probes together in a DNA probe sandwich hybridization assay (schematic shown in FIG. 3). The assay was carried out as described by Van Ness and Chen et al. (1991) supra.; Van Ness et al. (1991) supra.]. Briefly, the assay involves the following major steps:

1. rRNA capture. Nylon beads with tethered probe MTB002 were added to samples of the lysate containing approximately $1 \times 10^9$ lysed cells. Both precursor and mature 16S rRNA in the lysate was captured on the nylon beads by hybridization with MTB002. Hybridization was performed at room temperature.

2. Pre-rRNA labeling. The lysate solution containing uncaptured nucleic acid and other materials was removed by aspiration, and a solution containing 5 µg/ml MTB030-biotin was added. The biotinylated MTB030 probe hybridized to captured rRNA molecules carrying precursor tails (pre-rRNA), resulting in a sandwich of CAPTURE BEAD : MTB002 : PRE-rRNA : MTB030 : BIOTIN.

3. Washes and detection. The sandwich was washed several times with a wash solution (50 mM HEPES pH 7.5, 100 mM NaCl, 0.5% w/v gelatin (Norland, Inc.)) to remove unhybridized nucleic acid and signal probes, and exposed to a solution of streptavidin-alkaline phosphatase conjugate (Vector Labs, Burlingame Calif.) diluted 1:1000 in the above-mentioned wash solution. The streptavidin-enzyme conjugate attached to the captured biotin molecules. After more washes to remove free conjugate, the sandwich was detected by incubation of the beads in substrate solution containing 100 µl Lumiphos 530 (Lumigen, Inc., Southfield, Mich.). Conversion of the chemiluminescent substrate by captured alkaline phosphatase was measured using a luminometer.

Results

When MTB030 was used as a signal probe, a significant signal was observed (FIG. 4). For comparative purposes, we ran a parallel assay using MTB034 (5'-GGCCAAAAATAACAACAAAAATGTGAAACC-3') (SEQ. ID NO:75) as a signal probe. This probe recognizes a different portion of the 5' pre-16S rRNA tail, starting 96 nucleotides upstream of the mature rRNA 5' terminus. No signal was observed using MTB034, suggesting that the region of the pre-rRNA to which MTB034 binds is double-stranded under the conditions employed in this assay. Therefore, access of MTB034 to the target is impeded.

This Example demonstrates the usefulness of probes that target single-stranded regions of the pre-rRNA. A partial list of target sequences in *M. tuberculosis* pre-rRNA that function well under the non-denaturing conditions employed in this experiment is presented in Table 2. Target sequences for pre-rRNA of other mycobacterial species are presented in Table 3.

The probes listed in Tables 2 to 4 provide strong signals in combination with a variety of different capture probes for mature rRNA sequences. Positive results are also obtained when the sandwich is reversed, such that the capture probe is specific for pre-rRNA tail sequences, and the signal probe hybridizes to sequences within the mature rRNA. Some of these oligonucleotide probes hybridized to regions not thought to be single stranded, according to published models for mycobacterial pre-rRNA secondary structure based upon DNA sequence analysis [Kempsell et al. (1992) supra.; Ji et al. (1994), supra.]. Thus, the binding of these probes under denaturing conditions was not expected.

Also unexpected was the good performance of probes MTB015 and MTB016, which target the 5' tail of the pre-23S rRNA. When used in combination with a capture probe specific for single-stranded regions of the mature 23S subunit, these probes gave the same or better sensitivity than probes for the pre-16S rRNA. This was unexpected in light of published data on processing of the 23S rRNA in other bacteria. For example, it has been reported that pre-23S rRNA is much less abundant than pre-16S rRNA in *E. coli*, presumably due to more rapid processing of the larger rRNA subunit [King et al. (1983) *J. Biol. Chem.* 258: 12034–12042]. It appears from our results that this is not the case in the slow-growing mycobacteria.

As does Example 3, this Example demonstrates that the claimed methods can rapidly evaluate mycobacterial response to rifampin and other antimicrobial compounds that inhibit RNA synthesis or processing, and to detect strains that are resistant to these compounds. Because this method does not require extraction and purification of the pre-rRNA prior to hybridization, it is a particularly convenient way to detect pre-rRNA.

Example 5

Evaluation of mycobacterial response to antimicrobial agents by quantitation of cellular pre-rRNA To demonstrate that one can rapidly quantitate antibiotic sensitivity of a mycobacterial sample, we used a nonpathogenic Mycobacterium species, *M. smegmatis*, as a model. This organism is naturally resistant to rifampin, so we examined the effects on pre-rRNA of two protein synthesis inhibitors, chloramphenicol and kanamycin. Rifampin, which we used in the previous Examples, works by inhibiting pre-rRNA synthesis while allowing processing to proceed. Chloramphenicol has the opposite effect, inhibiting pre-rRNA processing without affecting synthesis. Thus, one would expect pre-rRNA levels to increase in chloramphenicol-sensitive cells.

We cultured *M. smegmatis* for two days on Middlebrook 7H9 broth (PML Microbiologicals). On the third day, the culture was split into three tubes. Chloramphenicol was added to one tube to a final concentration of 100 µg/ml, kanamycin was added to the second tube to 100 µg/ml, and the third tube was left untreated. Cultures were incubated for an additional two hours, or about one half the normal generation time for *M. smegmatis* under these conditions.

At the end of this period, we lysed samples of each culture containing about $3 \times 10^8$ cells using the enzymatic method (Table 1c). Chloramphenicol or kanamycin was present in all solutions used in the lysis procedure to prevent processing of pre-rRNA during lysis. We detected pre-rRNA using a chemiluminescent sandwich assay similar to that described in Example 4. We used as a capture probe MSM001 (5'CGGCTCCCTCCACAAGGGTTAGGCCACC3')(SEQ. ID NO:76), which recognizes an open region within the mature rRNA of M. smegmatis,. The signal probe was MSM008 (5'TCACACCCTCCCCAACGGA3')(SEQ. ID NO:77), which recognizes an open region in the 3'pre-16S precursor tail of this organism.

The results of this experiment are shown in Table 6. Although the brief antibiotic treatment had no effect on culture turbidity or other visible aspects of culture density, it had a measurable and reproducible effect on pre-rRNA concentration as measured by the chemiluminescent sandwich assay.

TABLE 6

Effects of antibiotic treatment on pre-rRNA copy number in *M. smegmatis*

| Treatment | Culture density | pre-rRNA/ml (luminometer units) |
|---|---|---|
| None | $3 \times 10^8$ cells/ml | 6.0 |
| Kanamycin | $3 \times 10^8$ cells/ml | 22.5 |
| Chloramphenicol | $3 \times 10^8$ cells/ml | 41.9 |

Using *E. coli* as a model, we observed similar 5- to 7-fold increases in pre-rRNA copy number in response to chloramphenicol and kanamycin treatment (data not shown). The data presented here support the assumption that processing pathways for the mycobacterial and *E. coli* 16S rRNA are similar.

Rifampin treatment can be expected to have an opposite, and even more dramatic, effect compared to kanamycin. In Example 1, we demonstrated that rifampin causes more than a 100-fold decrease in *E. coli* pre-rRNA copy number within one generation time of exposure to the drug. *M. tuberculosis*, is also very sensitive to rifampin [Heifets (1988) *Am. Rev. Respir. Dis.* 137: 1217–1222]. Therefore, pre-rRNA in rifampin-sensitive *M. tuberculosis* will also decrease in response to rifampin. Similarly, other antimicrobial agents will cause similar effects by directly or indirectly inhibiting pre-rRNA synthesis or processing. Such effects would not be observed in strains that are resistant to the drugs.

Example 6
Amplification of pre-rRNA using in vitro RNA amplification methods

Mycobacterial samples are treated with the antibiotics being tested for 2 hours. Control samples not challenged with antibiotics are tested in parallel. After the incubation period, the cells are lysed and the pre-rRNA freed from the cells using the enzymatic lysis protocol described in Table 1c. Selected portions of the precursor rRNA are amplified using primer sets that include at least one primer specific for pre-rRNA sequences. The second primer in the set hybridizes to either neighboring pre-rRNA sequences, or to nearby sequences within mature rRNA. Preferably, the primers selectively hybridize to regions of the pre-rRNA or mature rRNA that lack significant secondary structure (such as intramolecular duplexes).

The amount of pre-rRNA amplification product present in each sample is determined using a chemiluminescent sandwich assay as described in Example 4. An increase or decrease in the levels of pre-rRNA-specific amplification product in antibiotic-treated cells relative to untreated cells is indicative of sensitivity to the antibiotic. The amplification step greatly increases assay sensitivity, permitting the clinician to carry out assays using very small numbers of mycobacterial cells, such as those found in an uncultured sample from a patient.

Example 7
Rapid assessment of the susceptibility of *Mycobacterium tuberculosis* to antituberculosis drugs.

The rapidity of in vitro antibiotic susceptibility testing is limited by the time it takes to visualize the physiological effects of antibiotics on cultured pathogens. Slow-growing pathogens such as *Mycobacterium tuberculosis*, which even under ideal culture conditions takes up to a day for each cell division, can require two weeks or more of culture in the presence of a drug before the physiological effects become visible. As illustrated in the present example, measurements of pre-rRNA content can shorten this time considerably. By hybridizing extracted *M. tuberculosis* H37Ra nucleic acid to a radiolabeled oligonucleotide probe specific for *M. tuberculosis* pre-16S rRNA tail sequences, we detected clear responses to rifampicin and ciprofloxacin within 3 hours and 48 hours, respectively, of in vitro antibiotic exposure.

*M. tuberculosis* strain H37Ra (ATCC 25177) was cultured on Dubos broth with albumin enrichment (Difco Laboratories, Detroit, Mich.) to an optical density at 600 nanometers ($OD_{600}$) of 0.2–0.4. Cells were diluted 5-10 fold in 75 ml of fresh broth (final OD600=0.04–0.05) in fluted 250 ml culture flasks. Rifampicin or ciprofloxacin (Sigma Chemical Co., St. Louis, Mo.) were added to a final concentration of 5 ug/ml, and control cultures were left untreated. Cultures were incubated with gentle agitation under air at 37° C., and additional samples were taken after approximately 3 hours, 7 hours, 24 hours, and 48 hours.

Immediately prior to antibiotic addition and at several time points thereafter, culture optical density was measured and samples were taken as follows. Ten milliliters of each culture was centrifuged at low speed to pellet the cells, and the pellets were resuspended in approximately ⅙ volume of TE buffer. Guanidinium lysates were prepared as described in Table 1c "Rapid enzymatic method", except that proteinase K was used at 0.01 mg/ml, and both enzymes were added to TE prior to resuspending the cells. The lysates were stored frozen until use.

Nucleic acid was extracted from 0.2 ml of each lysate by phenol-chloroform extraction, and applied to 0.22 micron Magna NT membrane filters (MSI, Westboro, Mass.) using a slot blot apparatus as described by Moncla et al. (*J. Clin. Microbiol.* 28: 324–327, 1990). For the purposes of this demonstrative experiment, each sample was divided between two filters which were in turn cut in half before hybridization to probes, resulting in four replicate blotted samples per 0.2 ml of lysate. This corresponded to the application of nucleic acid from approximately $10^7$ cells per blot, assuming that a culture $OD_{600}$ of 1.0 corresponds to $10^9$ cells per milliliter.

Synthetic oligonucleotide probe MTB030 (5'-ACC CAA ACA CTC CCT TTG GAA AAG GG-3')(SEQ. ID NO:82) was used to detect *M. tuberculosis* pre-16S rRNA in slot blot hybridization assays. For comparison, we also used probe UP041 (5'-CTG CTG CCT CCC GTA GGA GT-3')(SEQ. ID NO:85), which recognizes a conserved region within the mature 16S rRNA, to quantitate combined precursor and mature 16S rRNA. Since less than 10% of total bacterial rRNA is typically in the precursor form (King et al., *J. Biol. Chem.*, 258: 12034–12042, 1983), relative signal with this probe primarily reflects mature rRNA copy number. For the purpose of demonstration we also used probe MTB030r, the complement of MTB030, to detect the chromosomal rrn operon (DNA) sequence coding for the pre-16S rRNA. Oligonucleotide probes were synthesized and end-labeled with $^{32}P$ using polynucleotide kinase (Moncla et al., 1990). Hybridizations were carried out either at room temperature in a 3M guanidinium thiocyanate hybridization solution, or at 42° C. in a formamide/SDS/Denhardt's solution (Moncla et al., 1990). Filters were washed at 52° C. in 9 mM Tris pH 8.0, 90 mM NaCl, 0.6 mM EDTA, and 0.2% SDS, and exposed to X-Omat autoradiography film.

Figure 5A:
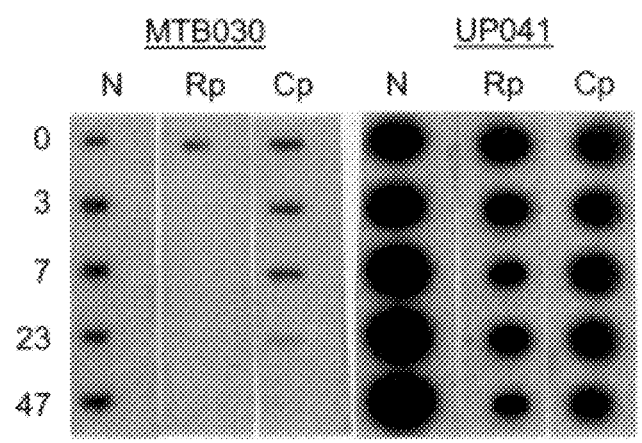
FIGS. 5A and 5B. Assessment of mycobacterial response to rifampicin and ciprofloxacin. Replicate cultures were exposed to the antibiotics or left untreated, and samples taken as described in Example 7. 5A., Slot blot hybridization assays for pre-16S rRNA detected by probe MTB030, and combined precursor and mature 16S rRNA detected by probe UP041. Time in hours after addition of antibiotics is shown to the left. N, no treatment; Rp, rifampicin; Cp, ciprofloxacin. 5B., Culture density (optical density at 600 nm) of the same cultures at the same time points. Squares, no treatment; circles, rifampicin; triangles, ciprofloxacin. Identical results were obtained in replicate experiments.
Figure 5B:
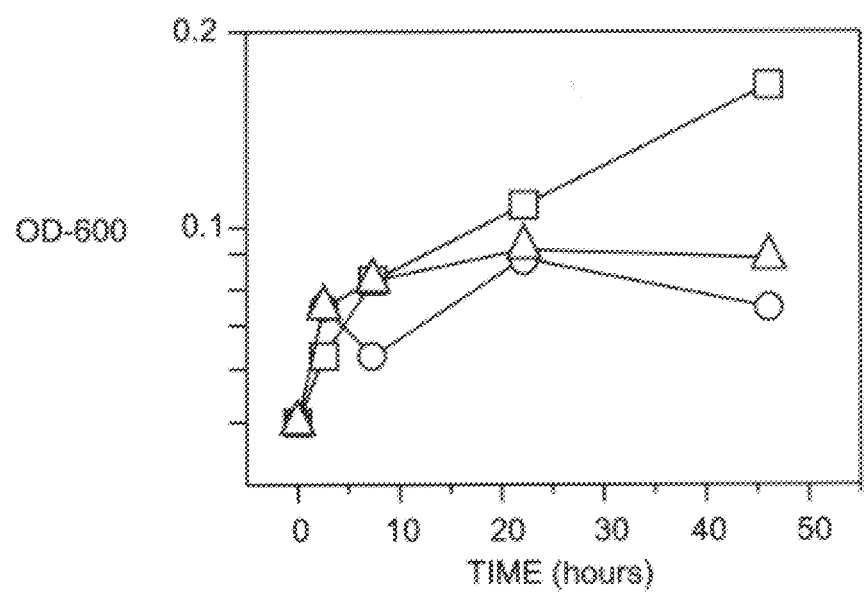

The following results were obtained. *M. tuberculosis* pre-rRNA detected by probe MTB030 remained almost constant in untreated cultures, but decreased to nearly undetectable levels after only 3 hours of rifampicin treatment and 48 hours of ciprofloxacin treatment (FIG. 5A). Over the short time course of this experiment the divergence in pre-rRNA content between treated and untreated cultures was far greater than the divergence in traditional measurements of cell mass and viability, inclung mature rRNA content measured by probe UP041 (FIG. 5A), and culture optical density (FIG. 5B). One skilled in the art would predict that strains which are resistant to these drugs would not exhibit this depletion in pre-rRNA levels over the same periods, and would thus be readily distinguishable from sensitive strains.

Figure 6:
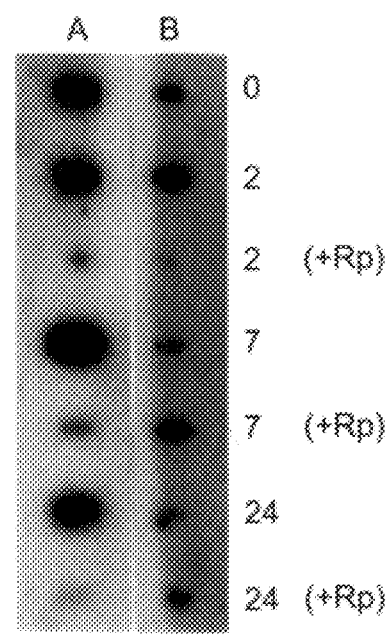
FIG. 6. Comparison of (A) pre-16S rRNA detected by probe MTB030, and (B) the DNA sequence encoding pre-16S rRNA detected by complementary probe MTB030r, in slot blot hybrid-ization assays. Replicate cultures were exposed to rifampicin (+Rp) or left untreated as described in Example 7. Time in hours after addition of the antibiotic is shown to the right.

In all experiments of this type, antibiotic treatment decreased pre-rRNA to barely detectable levels which then remained constant over time. This "background" may have been due to residual pre-rRNA, or to hybridization of the probe to the chromosomal rrn operon DNA coding for the pre-rRNA. To test the latter possibility with the greatest possible sensitivity, parallel cultures of *M. tuberculosis* were treated with rifampicin or left untreated as described above, except that the experiment was carried out at approximately five times the cell concentration. Replicate filters were hybridized to MTB030 and its complement, MTB030r, which is specific for the coding strand of the rrn operon DNA. After extended autoradiography to clearly reveal background signal, MTB030 signal did not measurably exceed MTB030r signal in nucleic acid extracted from rifampicin-treated cells (FIG. 6). Similar results were obtained when replicates of the filters shown in FIG. 5 were hybridized to MTB030r and overexposed (data not shown). These data suggest that pre-rRNA copy number in rifampicin-treated cells does not measurably exceed that of the DNA encoding it.

Our results show that pre-rRNA levels respond extremely rapidly to certain antibiotics, making pre-rRNA an attractive physiological indicator of antibiotic susceptibility in the slow-growing mycobacteria. The "background" contributed by hybridization of probes to DNA rrn operon sequences could be greatly reduced or eliminated by hybridizing to DNA probes in the presence of chaotropic trichloroacetate salts, which favor DNA:RNA interactions over DNA:DNA interactions (Van Ness and Chen, *Nucl. Acids Res.* 19: 5143–5151, 1991). Alternatively, the DNA could be selectively degraded using deoxyribonucleases.

It will be apparent to one skilled in the art that sensitivity of this assay for pre-rRNA could be improved somewhat by using longer probes and more sensitive labeling methods, and to a much greater extent by using in vitro RNA amplification techniques such as NASBA or reverse transcriptase PCR, as described in Example 6. Such amplification would allow clinicians to apply our invention directly on patient samples after brief experimental antibiotic challenge, or on young enrichment cultures. This approach could yield antibiotic susceptibility data within 1 to 3 days of obtaining a sputum sample, a significant improvement over current methods. Moreover, the specificity of DNA probes for pre-rRNA would allow the procedure to be carried out on mixed microbial populations such as unpurified patient samples.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for determining whether cells of a mycobacterial sample are sensitive to an antimicrobial agent, the method comprising the steps of:
  (a) culturing the mycobacterial cells in the presence of the antimicrobial agent;
  (b) treating the cells by enzymatic or mechanical means to expose the cell membrane to lysis reagents, and contacting the cells with a lysis reagent under conditions that release but do not degrade pre-rRNA from the mycobacterial cells; and
  (c) detecting the pre-rRNA using an oligonucleotide probe which is capable of selectively hybridizing, under hybridizing conditions, to a region of the pre-rRNA that is not present in a mature mycobacterial rRNA molecule;

wherein sensitivity to the antimicrobial agent is indicated by an increase or a decrease in pre-rRNA levels for mycobacterial cells exposed to the antimicrobial agent compared to mycobacterial cells not exposed to the antimicrobial agent.

2. A method of claim 1 wherein the antimicrobial agent is rifampin.

3. A method for determining the antimycobacterial efficacy of a compound, the method comprising the steps of:
  (a) incubating mycobacterial cells in the presence of the compound,
  (b) treating the cells by enzymatic or mechanical means to expose the cell membrane to lysis reagents, and contacting the cells with a lysis reagent under conditions that release but do not degrade pre-rRNA from the mycobacterial cells; and
  (c) detecting the pre-rRNA using an oligonucleotide probe which is capable of selectively hybridizing, under hybridizing conditions, to a region of the pre-rRNA that is not present in a mature mycobacterial rRNA molecule;

wherein sensitivity to the compound is indicated by an increase or a decrease in pre-rRNA levels for mycobacterial cells exposed to the compound compared to mycobacterial cells not exposed to the compound.

4. A method of claim 3 wherein the cells are depleted of pre-rRNA prior to contact with the compound.

5. A method of claim 4 wherein the cells are depleted of pre-rRNA by limiting a nutrient.

6. A method of claim 4 wherein the cells are depleted of pre-rRNA by exposing the cells to a second antibiotic compound which is other than the test compound and removing the second compound prior to contact with the test compound.

* * * * *